(12) United States Patent
Okada et al.

(10) Patent No.: US 7,019,104 B1
(45) Date of Patent: *Mar. 28, 2006

(54) DIAMINE NOVEL ACID DIANHYDRIDE AND NOVEL POLYIMIDE COMPOSITION FORMED THEREFROM

(75) Inventors: Koji Okada, Shiga (JP); Shoji Hara, Shiga (JP); Hitoshi Nojiri, Shiga (JP)

(73) Assignee: Kaneka Corporation, Osaka (JP)

(*) Notice: Subject to any disclaimer, the term of this patent is extended or adjusted under 35 U.S.C. 154(b) by 463 days.

This patent is subject to a terminal disclaimer.

(21) Appl. No.: 10/129,036

(22) PCT Filed: Nov. 1, 2000

(86) PCT No.: PCT/JP00/07714

§ 371 (c)(1),
(2), (4) Date: Apr. 30, 2002

(87) PCT Pub. No.: WO01/32749

PCT Pub. Date: May 10, 2001

(30) Foreign Application Priority Data

Nov. 1, 1999 (JP) .................. 11-311718
Jan. 17, 2000 (JP) .................. 2000-008390
Jan. 17, 2000 (JP) .................. 2000-008391

(51) Int. Cl.
C07C 229/44 (2006.01)
C07C 229/60 (2006.01)
C08G 73/10 (2006.01)
C07D 307/89 (2006.01)

(52) U.S. Cl. ............ 528/229; 528/220; 528/310; 560/49; 560/50; 560/55; 560/104

(58) Field of Classification Search ............ 528/353; 560/104
See application file for complete search history.

(56) References Cited

U.S. PATENT DOCUMENTS

| 4,851,562 | A | * | 7/1989 | de Jonge et al. ............ 560/19 |
| 6,303,742 | B1 | * | 10/2001 | Okada et al. ............ 528/353 |
| 6,689,899 | B1 | * | 2/2004 | Okada et al. ............ 560/104 |
| 6,790,930 | B1 | * | 9/2004 | Kikuchi et al. ............ 528/353 |
| 2002/0019558 | A1 | * | 2/2002 | Okada et al. ............ 560/49 |

FOREIGN PATENT DOCUMENTS

| JP | 3-59031 | 3/1991 |
| JP | 3-59034 | 3/1991 |
| JP | 5-1224 | 1/1993 |
| JP | 5-86183 | 4/1993 |
| JP | 5-331116 | 12/1993 |
| JP | 9-90629 | 4/1997 |
| JP | 2000-281783 | 10/2000 |
| WO | WO 91/03001 | 3/1991 |
| WO | WO 99/51662 | 10/1999 |

OTHER PUBLICATIONS

International Search Report Corresponding to International Application No. PCT/JP00/07714 From Japanese Patent Office Dated Feb. 6, 2001, 2 Pages.

* cited by examiner

Primary Examiner—P. Hampton Hightower
(74) Attorney, Agent, or Firm—Brinks Hofer Gilson & Lione

(57) ABSTRACT

An object of present invention is to provide a diamine and an acid dianhydride having photoreactivity and thermoreactivity and a polyimide composition containing the diamine and the acid dianhydride as monomer components, and specifically to synthesize a diamine and an acid dianhydride having a photoreactive and thermoreactive group containing a double bond or triple bond such as cinnamic acid, chalcone, benzalacetophenone, stilbene, coumarin, pyrone, allyl, propargyl, and acetylene or a derivative skeleton thereof so as to exhibit photoreactivity and thermoreactivity specific to the reactive group, thereby providing a polyimide composition containing the diamine and the acid dianhydride.

11 Claims, No Drawings

DIAMINE NOVEL ACID DIANHYDRIDE AND NOVEL POLYIMIDE COMPOSITION FORMED THEREFROM

RELATED APPLICATIONS

This application is a nationalization of PCT application PCT/JP00/07714 filed Nov. 1, 2000. This application claims priority from the PCT application and Japan Application Serial No. 11-311718 filed Jan. 11, 1999; Japan Application Serial No. 2000-8390 filed Jan. 17, 2000; and Japan Application Serial No. 2000-8391 filed Jan. 17, 2000.

FIELD OF THE INVENTION

The present invention relates to a novel diamine, novel acid dianhydride, and novel polyimide containing them, and more particularly to a novel photoreactive and thermoreactive diamine and acid dianhydride derived from a reactive group containing a double bond or triple bond and a novel polyimide containing the novel diamine and acid dianhydride as monomer components and having both photoreactivity and thermoreactivity specific to the reactive group.

BACKGROUND OF THE INVENTION

Polyimides have been widely used, for example, in the field of electronic communication and OA appliances as well as in the field of aerospace because they have excellent heat resistance among a variety of organic polymers. In particular, the polyimides have recently been desired to have not only excellent heat resistance but also a variety of performance for a wide range of uses.

Photosensitive polymers can be obtained by a reaction of existing polymers and photosensitive groups functioning as pendant groups. A representative example of the photosensitive polymers prepared by this method is polyvinyl cinnamate invented by Minsk et al., which is disclosed in J. Appl. Polymer Sci., 2, 302 (1959). Polyvinyl cinnamate is prepared by the esterification of polyvinyl alcohol using cinnamic acid chloride. This polymer is irradiated with light to form cyclobutane rings to be cross-linked and cured.

However, to the inventors' knowledge, polyimides with a derivative of cinnamoyl skeleton joined to their side chains is reported only in Japanese Unexamined Patent Publication No. (Patent Kokai No.)$_{55}$-45747 (1980). The polyimide disclosed in the Patent Kokai No. 55-45747 contains, as a diamine monomer component, aromatic diamine in which an amino group and one or two photosensitive group(s) such as cinnamic acid derivative are bonded to the same aromatic residue.

Although a polymer into which a reactive group having a double bond or triple bond is introduced may be used as thermosetting resins, there have been few cases where polyimides are used as thermosetting resins by introducing such thermoreactive group thereto.

Furthermore, although an increase in number of reactive groups per polymer repeating unit increases a cross-linking density and improves properties, there have been few cases where polyimide contains a multifunctional diamine as a monomer component.

An object of present invention is to provide a diamine and an acid dianhydride which have a reactive group containing a double bond or triple bond so as to exhibit both photoreactivity and thermoreactivity specific to the reactive group, and a polyimide containing the diamine and the acid dianhydride as monomer components.

SUMMARY OF THE INVENTION

The present inventors have studied intensively and found that their intended object can be achieved by preparing a diamine and an acid dianhydride of a special structure and polyimide containing such diamine and acid dianhydride as monomer components, and consequently they have accomplished the present invention.

An example of a diamine according to the present invention has 2 to 4 organic groups containing at least one double bond or triple bond, wherein a first organic group in which at least the two organic groups having at least one double bond or triple bond are bonded is bonded to a second and a third organic groups to which an amino group is bonded, by the medium of a divalent organic group selected from the group consisting of —O—, —CO—, —COO—, —OCO—, —NH—, —NHCO—, and —CONH—.

Another example of a diamine according to the present invention is a diamine having a structure represented by the following general formula (1) according to claim 1

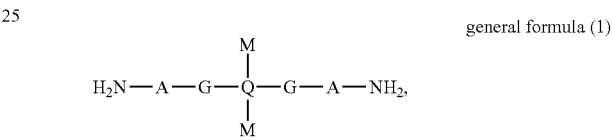

general formula (1)

wherein A and G each represent a divalent organic group, G is a divalent organic group selected from the group consisting of —O—, —CO—, —COO—, —OCO—, —NH—, —NHCO—, and CONH—, Q represents a tetravalent organic group, and M represents RCOO— or ROCO—, wherein R represents a monovalent organic group having the reactive group selected from the following group(II)

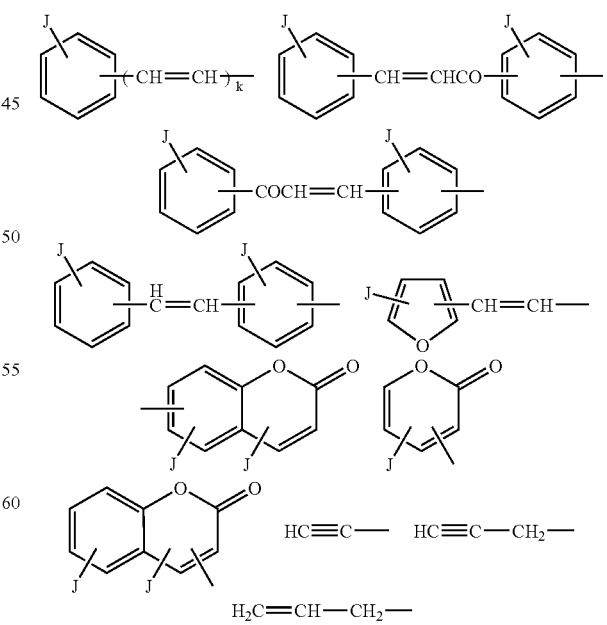

(wherein k is an integer of 1 or 2, J is a group capable of arbitrarily substituting for hydrogen atom of an aromatic ring and independently represents halogen, C1 to C3 alyl, C1 to C3 alkoxy, or C1 to C3 fluoroalkyl, or a combination thereof).

Further, in the above general formula (1), A may be a divalent organic group selected from the following group consisting of Group (I)

, wherein k is an integer of 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof.

Further, in the above general formula (1), Q may be a tetravalent aliphatic hydrocarbon group having 2 to 20 carbon atoms, and a tetravalent organic group selected from the group consisting of

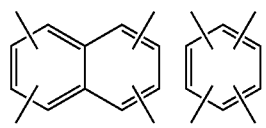

Further, in the above general formula (1), R may be a monovalent organic group selected from the following group (III) consisting of Group (III)

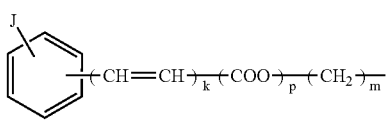

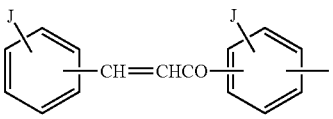

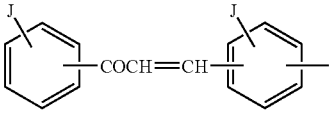

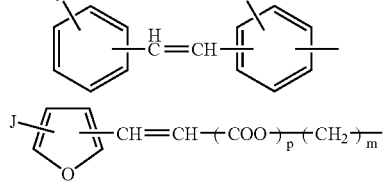

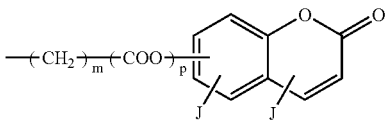

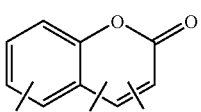, wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof, m is an integer of 0 to 20, p is 0 when m is 0 or 1, or p is 1 when m is 2 or more.

Further, a diamine of the present invention may be selected from the group consisting of the following compounds:

(10)
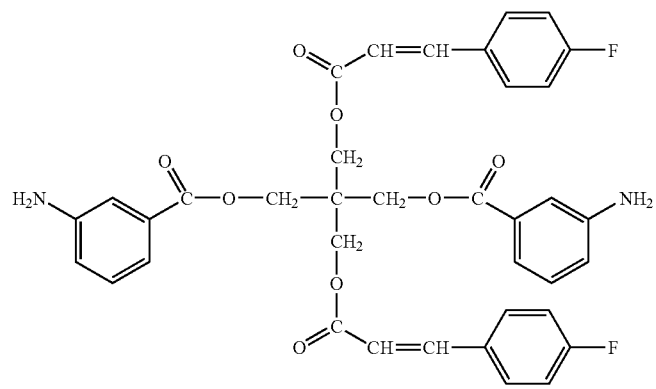
(11)
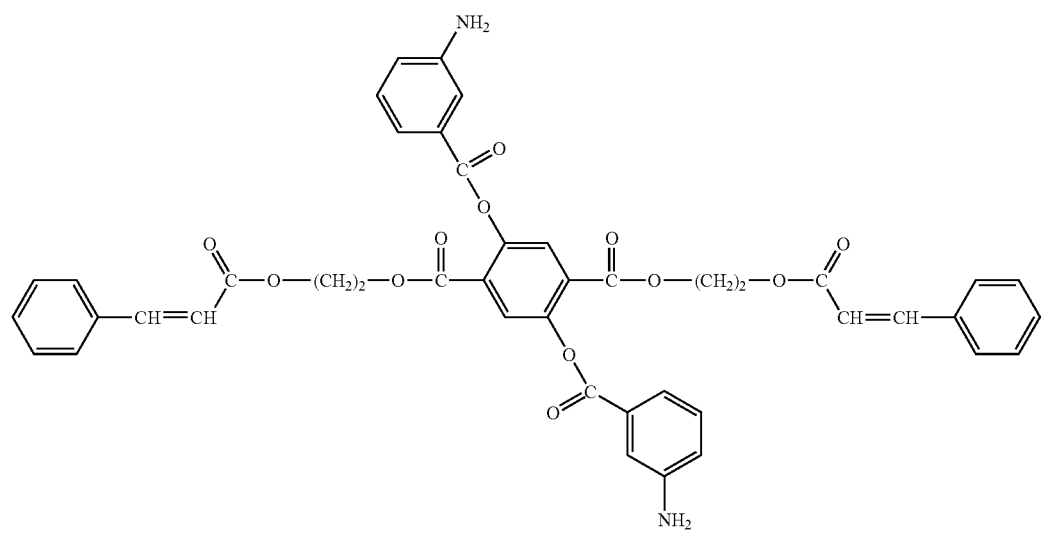
(12)
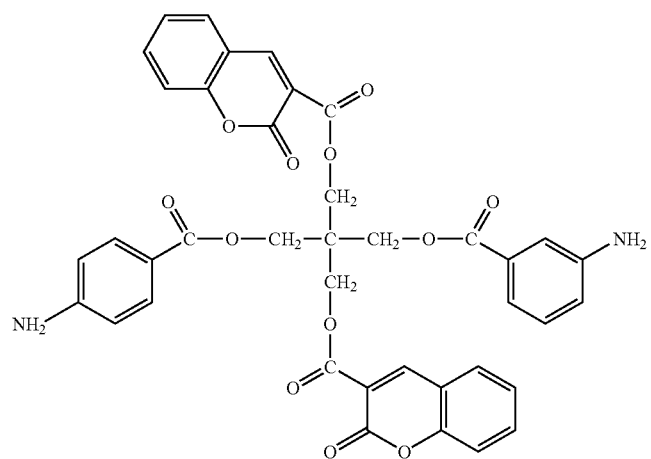

-continued

(13)
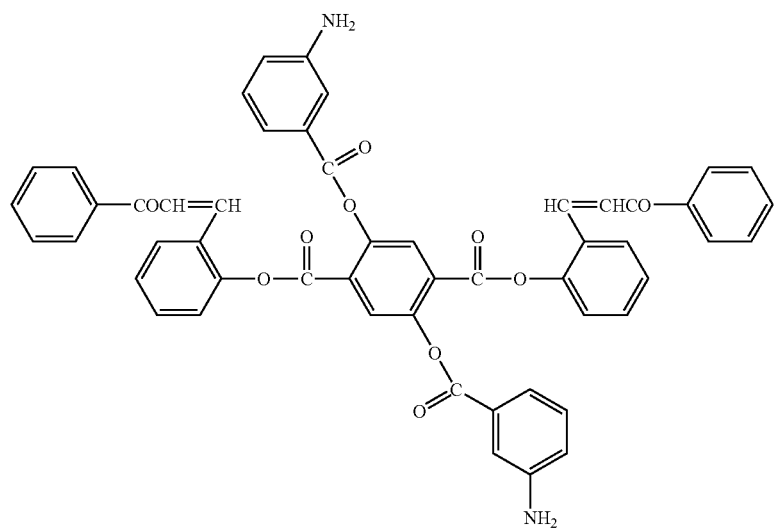

(14)
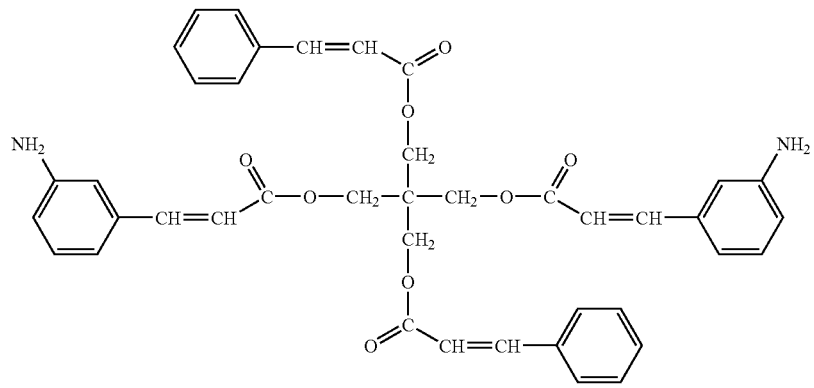

Further, another example of a diamine of the present invention is represented by the general formula (3):

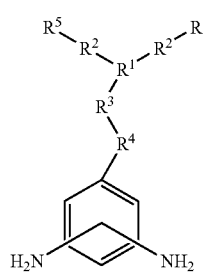

general formula (3)

(wherein $R^2$, $R^3$, and $R^4$ each represent a divalent organic group, $R^1$ represents a trivalent organic group, and $R^5$ represents a monovalent organic group having a reactive group derived from cinnamic acid, chalcone, benzalacetophenone, stilbene, coumarin, pyrone, allyl, propargyl, and acetylene.)

Further, in the general formula (3), $R^1$ may be $C_nH_{2n-1}$ (wherein n is an integer of 1 to 20), benzene ring, or naphthalene ring.

Further, in the general formula (3), $R^2$ may be a single bond, —COO—, —NHCO—, —$(C_mH_{2m})$COO—, or —OCO$(C_mH_{2m})$COO— wherein m is an integer of 2 to 20.

Further, in the general formula (3), $R^3$ may be a single bond and —COO—, $R^4$ may be —, —$CH_2$—, and —COO—.

Further, in the general formula (3), $R^5$ may include a monovalent organic group selected from the following group (II) consisting of Group (II)

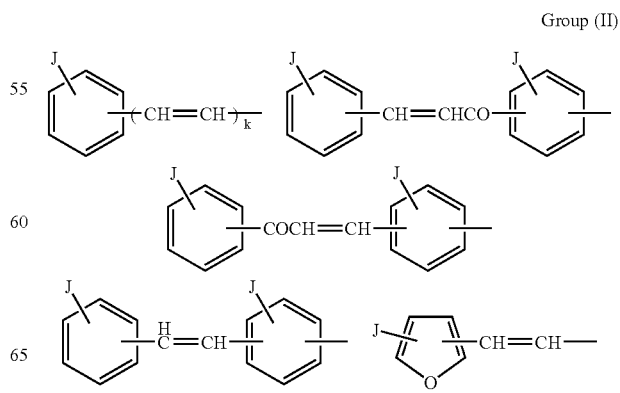

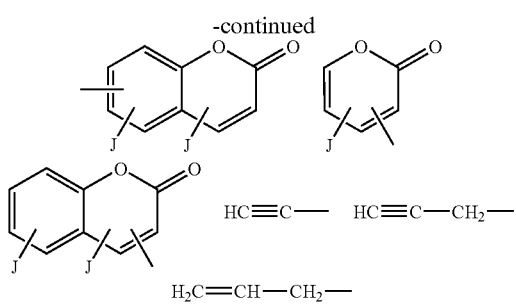

(wherein J is a group capable of arbitrarily substituting for hydrogen atom of an aromatic ring and independently represents halogen, C1 to C3 alyl, C1 to C3 alkoxy, or C1 to C3 fluoroalkyl, or a combination thereof.)

An acid dianhydride of the present invention is represented by the following general formula (5):

general formula (5)

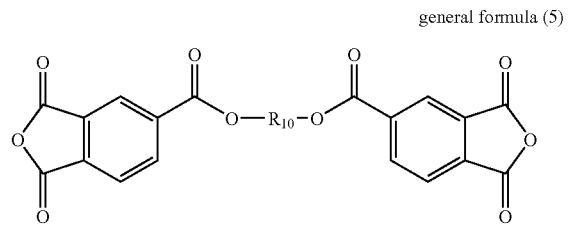

(wherein $R^{10}$ represents a divalent organic group having a reactive group derived from cinnamic acid, chalcone, benzalacetophenone, stilbene, coumarin, pyrone, allyl, propargyl, or acetylene).

Further, in the general formula (5), $R^{10}$ may be a divalent organic group selected from the following group (VII):

Group (VIII)

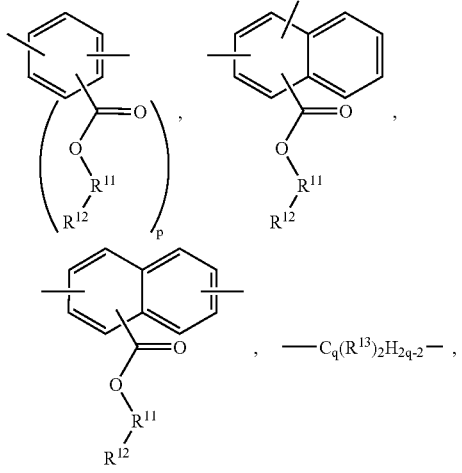

(VII)

(wherein $R^{11}$ represents a single bond, $-C_rH_{2r}OOC-$, $-C_rH_{2r}COO-$, $R^{12}$ and $R^{13}$ each represent a divalent organic group derived from cinnamic acid, chalcone, benzalacetophenone, stilbene, coumarin, pyrone, allyl, propargyl, and acetylene, q and r are an integer of 1 to 20, p is an integer of 1 or 2, and an ester bond is on the $R^{12}$ side when $R^{11}$ is $-C_rH_{2r}OOC-$, $-C_rH_{2r}COO-$).

Further, in the group (VII), $R^{12}$ may be selected from the following (II) group consisting of Group (II)

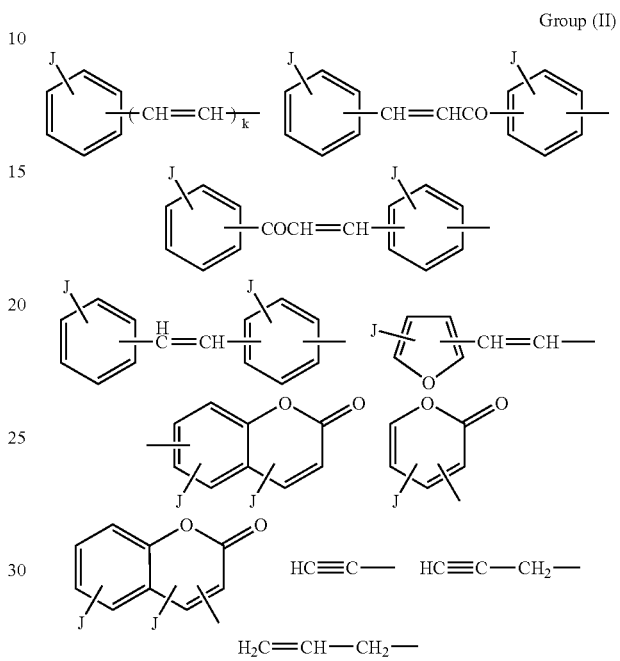

(wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof).

Further, in the group (VII), $R^{13}$ may be a monovalent organic group selected from the group (VIII):

(VIII)

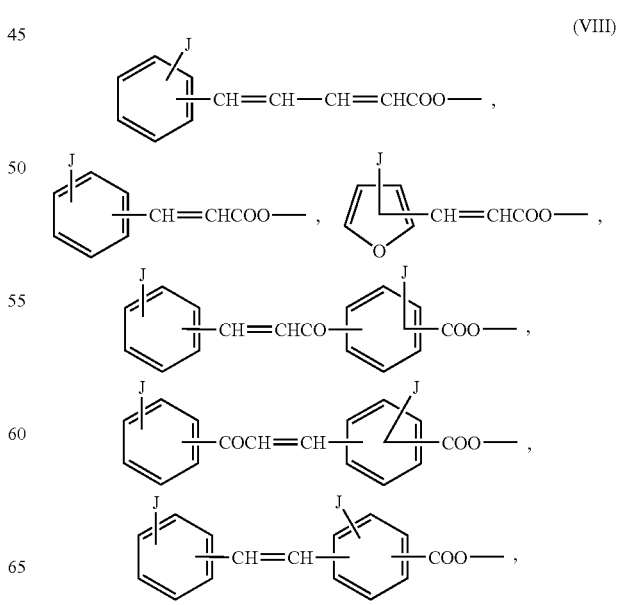

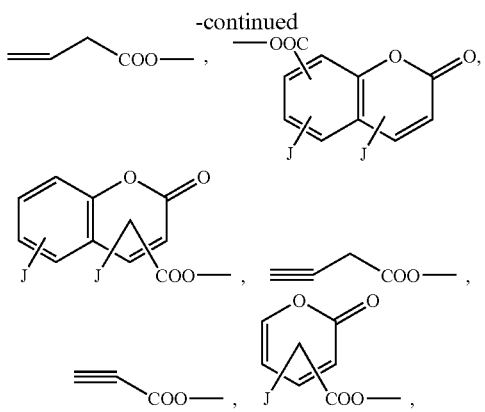

(wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof).

A polyimide composition of the present invention can be obtained by reacting a diamine including any of the aforementioned novel diamine with any acid dianhydride.

Alternatively, a polyimide composition of the present invention can be obtained by reacting an acid dianhydride including any of the aforementioned novel acid dianhydride with any diamine.

Further, a polyimide composition of the present invention has a repeating unit represented by the general formula (A)

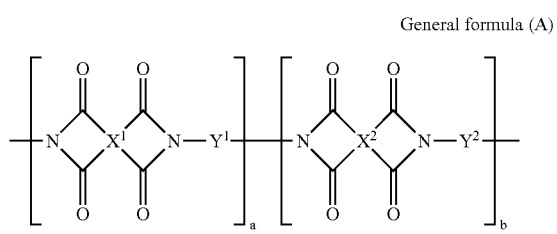

General formula (A)

(wherein $X^1$ and $X^2$ represent a tetravalent organic group and $Y^1$ and $Y^2$ represent a divalent organic group. At least one of $X^1$ and $X^2$ is selected from residues of the acid dianhydride represented by the general formula (5) and/or at least one of Y1 and Y2 is selected from residues of the diamine represented by the general formula (1) or (3)).

Further, a polyimide composition of the present invention may contain 1 wt % or more of repeating units represented by the following general formula (B):

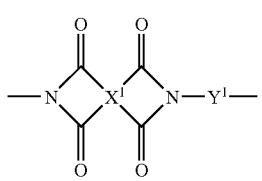

general formula (B)

(wherein $X^1$ represents a tetravalent organic group and $Y^1$ represents a diamine residue represented by the general formula (1):

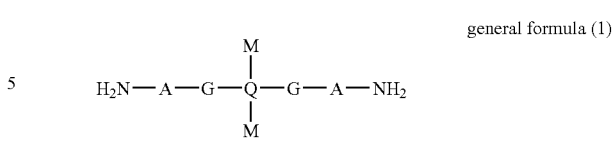

general formula (1)

or the general formula (3):

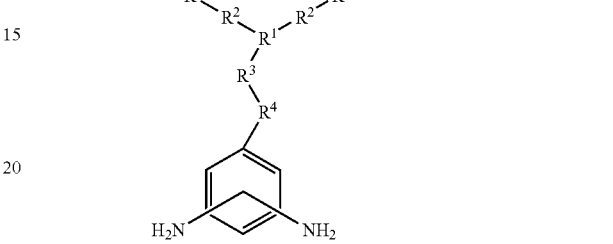

general formula (3)

Further, M in the general formula (1) and $R^5$ in the general formula (3) may be selected from the following group (II):

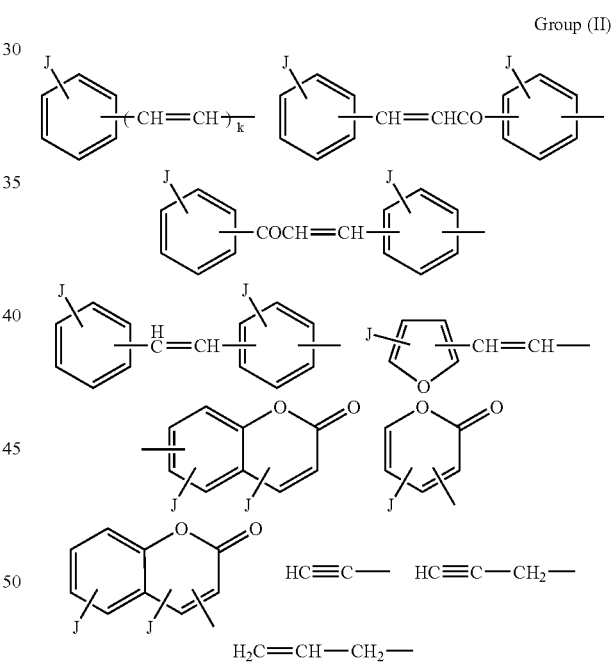

Group (II)

(wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof).

Further, in the polyimide represented by the general formula (A), $X^2$ may be one or more kinds of a tetravalent organic group having 1 to 3 aromatic rings or an alicyclic tetravalent organic group.

Further, a structure of a polyimide composition of the present invention may include 1 wt % or more of the following general formula (C):

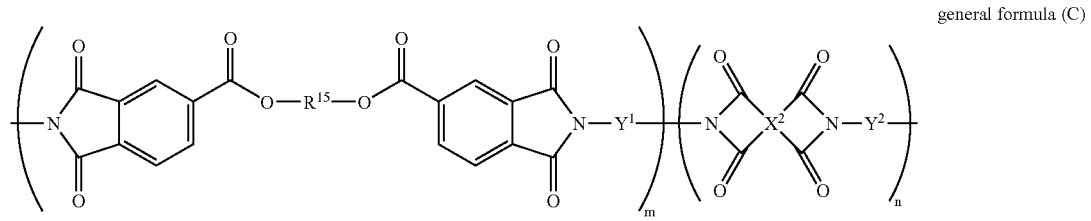

general formula (C)

(wherein $R^{15}$ is a divalent organic group containing a reactive group derived from cinnamic acid, chalcone, benzalacetophenone, stilbene, coumarin, pyrone, allyl, propargyl, and acetylene, $Y^1$ and $Y^2$ each are a divalent organic group, $X^2$ is a tetravalent organic group, m is an integer of one or more, n is an integer of 0 or more).

Further, in the general formula (C), $R^{15}$ may be a divalent organic group selected from the following group (VII):

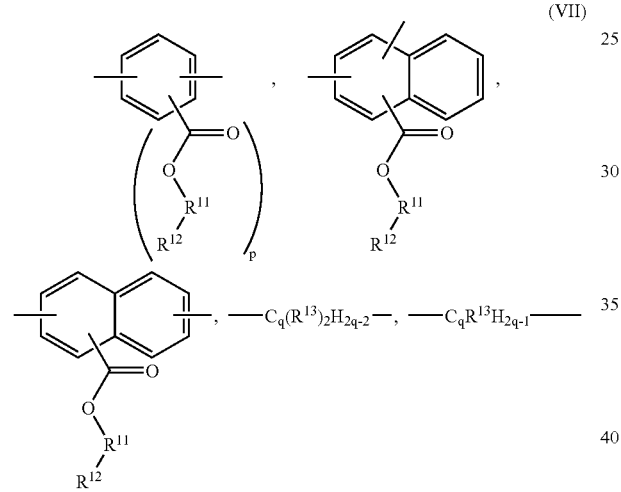

(VII)

(wherein $R^{11}$ represents a single bond, —$C_rH_{2r}$OOC—, or —$C_rH_{2r}$COO—, $R^{12}$ and $R^{13}$ each represent a divalent organic group derived from cinnamic acid, chalcone, benzalacetophenone, stilbene, coumarin, pyrone, allyl, propargyl, or acetylene, q and r are an integer of 1 to 20, p is an integer of 1 or 2, and an ester bond is on the $R^{12}$ side when $R^{11}$ is —$C_rH_{2r}$OOC— or —$C_rH_{2r}$COO—.

Further, in the group (VII), $R^{12}$ may be a monovalent organic group selected from the following group (II) consisting of:

Group (II)

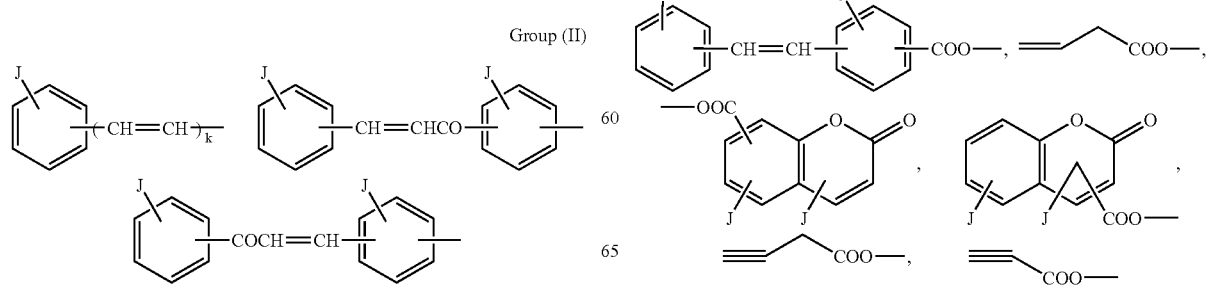

(wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof).

Further, in the aforementioned polyimide composition, $R^{13}$ may be a monovalent organic group selected from the following group (VIII) consisting of:

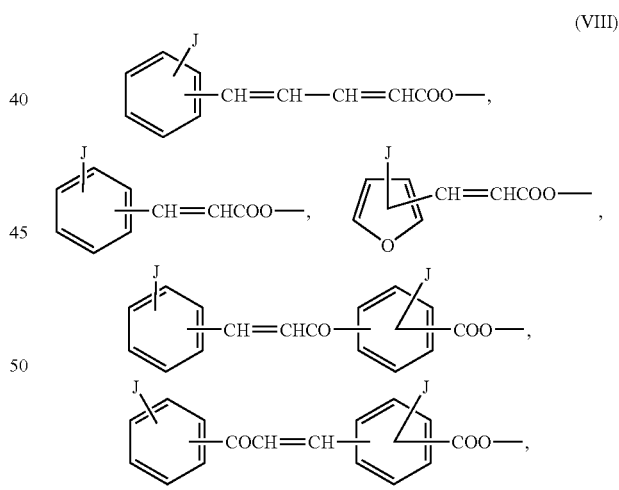

(VIII)

-continued

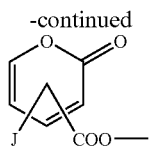

(wherein J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof).

DESCRIPTION OF THE PREFERRED EMBODIMENTS

In this specification, the term "organic group" is a part of an organic compound. It is typically a hydrocarbon group which may contain hetero atoms, and represents a group having elements which can be covalently bonded (the number of these elements are represented as the number of valences). The organic group may include an aliphatic group, alicyclic group, aromatic group, and hetero aromatic group. The size of the organic group is not particularly limited. The total number of carbon atoms of the organic group is typically C2 to C100, preferably C3 to C60, and more preferably C4 to C40.

In this specification, the term "reactive group having photoreactivity" means a reactive group capable of absorbing light and chemically reacting by the energy of the light. The kind of the light is not particularly limited. Examples of the light include visible light, ultraviolet light, and infrared light.

In this specification, the term "reactive group having thermoreactivity" means a reactive group capable of chemically reacting by the heat energy. The heat energy may be generally applied by heating.

The present invention will hereinafter be described in detail.

The present invention relates to a diamide and acid dianhydride containing a reactive group which has a double bond or triple bond and which shows photoreactive and the thermoreactive, and more particularly to a diamine and acid dianhydride which has a group derived from cinnamic acid, chalcone, benzalacetophenone, stilbene, coumarin, pyrone, allyl, propargyl, acetylene, and derivatives thereof and which has 2 to 4 organic groups containing a carbon—carbon double bond or carbon—carbon triple bond, and a polyimide formed by using such diamine and acid dianhydride. A first organic group in which at least the two organic groups are bonded is bonded to a second and third organic groups to which an amino group is bonded, by the medium of at least one hetero atom, respectively.

The diamine of the present invention may have a structure represented by the general formula (1):

general formula (1)

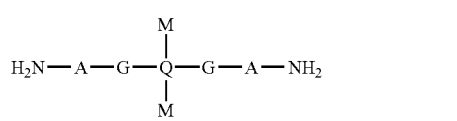

Following is an description of organic groups in the general formula (1).

A represents a divalent organic group independently.

(A-1)Preferably, A is a divalent organic group containing aromatic groups and/or hetero aromatic groups, and such aromatic groups and hetero aromatic groups may be monocyclic or bicyclic.

(A-2) More preferably, A is a divalent organic group selected from the group consisting of:

Group (I)

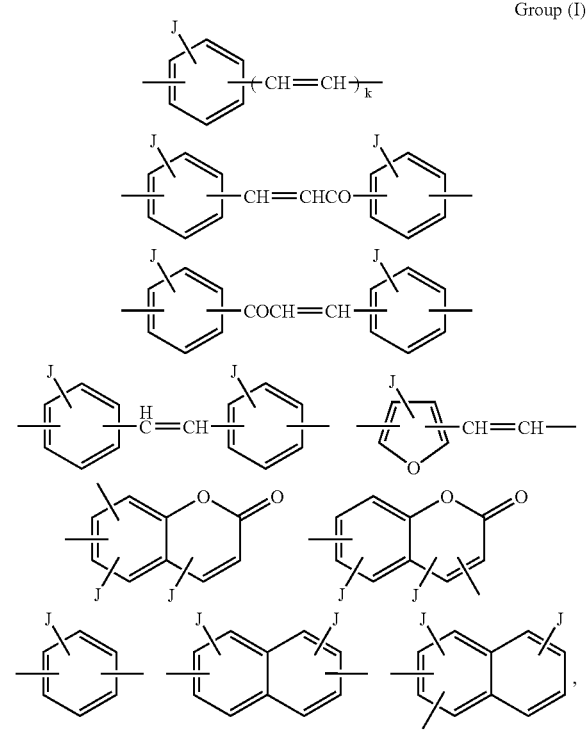

wherein k is 1 or 2, J is a group capable of arbitrarily substituting for hydrogen acorn of an aromatic ring and independently represents halogen, C1 to C3 alkyl, C1 to C3 alkoxy, or C1 to C3 fluoroalkyl, or a combination thereof. Examples of halogen include F, Cl, Br, and I, and a preferable halogen is F. Examples of C1 to C3 alkyl include methyl, ethyl, propyl, and isopropyl, and a preferable C1 to C3 alkyl is methyl. Examples of C1 to C3 alkoxy include methoxy, ethoxy, propoxy, and isopropoxy, and a preferable C1 to C3 alkoxy is methoxy. Examples of C1 to C3 fluoroalkyl include trifluoromethyl, tetrafluoroethyl, and heptafluoropropyl, and a preferable C1 to C3 fluoroalkyl is trifluoromethyl.

(A-3)More preferably, A is selected from the group consisting of:

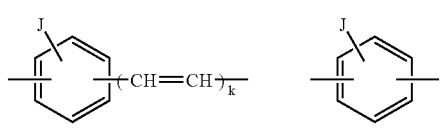

G represents a divalent organic group independently.

(G-1)Preferably, G is a divalent organic group containing hetero atoms selected from oxygen and nitrogen.

(G-2)More preferably, G is a divalent organic group selected from the group consisting of —O—, —CO—, —COO—, —OCO—, —NH—, —NHCO—, and —CONH—. In the general formula (1), a left bond of G is bonded to A and a right bond thereof is bonded to Q.

(G-3)Most preferably, G is —COO—. Q represents a tetravalent organic group.

(Q-1)Preferably, Q is a tetravalent organic group having 2 to 20 carbon atoms.

(Q-2)More preferably, Q is a tetravalent organic group selected from the group consisting of a tetravalent aliphatic hydrocarbon group having 2 to 20 carbon atoms and

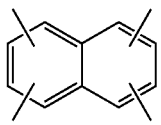

(Q-3) More preferably, Q is $c(CH_2)_4$ or

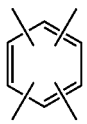

M represents RCOO— or ROCO—, wherein R represents a monovalent organic group having a reactive group and the reactive group may be an unsaturated hydrocarbon group containing at least one of an aromatic group and/or hetero aromatic group and a carbon—carbon double bond and/or carbon—carbon triple bond.

Preferably, R is a reactive group derived from cinnamic acid, chalcone, benzalacetophenone, stilbene, coumarin, pyrone, allyl, propargyl, and acetylene.

(R-1)Specifically, R is a monovalent organic group having a reactive group selected from the following group (II):

Group (II)

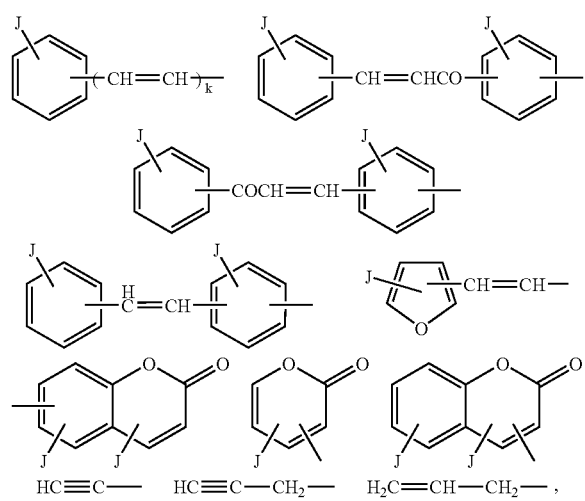

wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof. In the group (II), J is preferably a methyl group, methoxy group, and halogen.

(R-2)More preferably, R is a monovalent organic group selected from the group (III) consisting of Group (III)

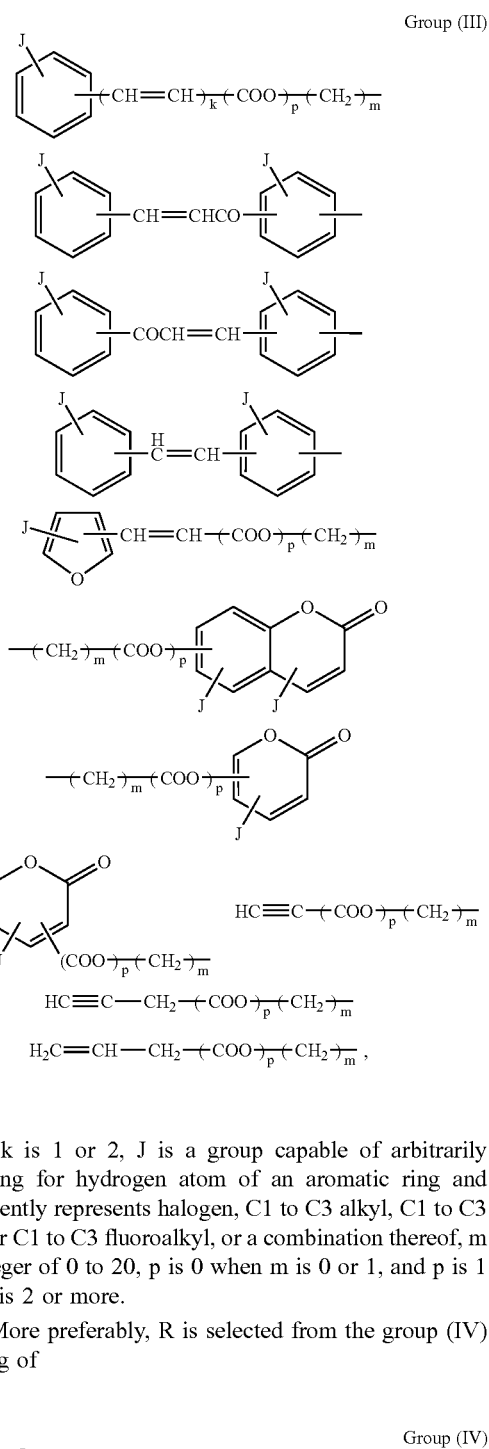

wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof, m is an integer of 0 to 20, p is 0 when m is 0 or 1, and p is 1 when m is 2 or more.

(R-3)More preferably, R is selected from the group (IV) consisting of

Group (IV)

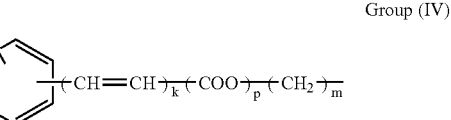

-continued

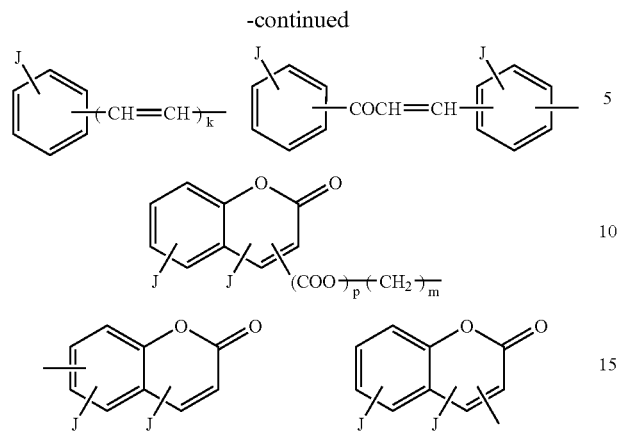

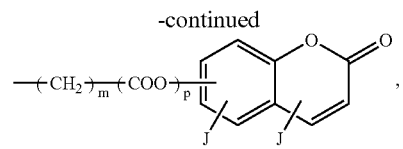

wherein K is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof, m is an integer of 2 to 10, and p is 1. Preferably, J is a methyl group, methoxy group, or halogen.

Particularly preferable diamine of the present invention represented by the general formula (1) may be selected from the group consisting of the following compounds (10) to (14):

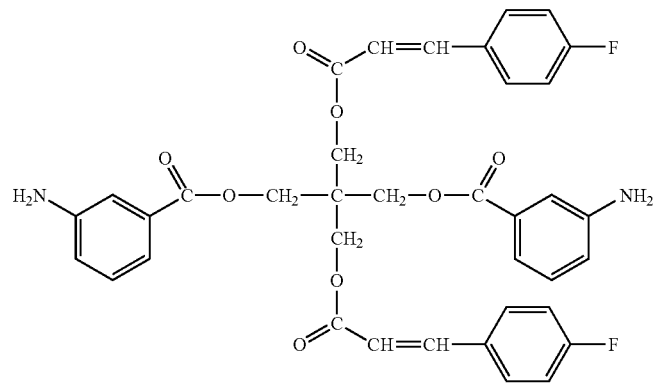

(10)

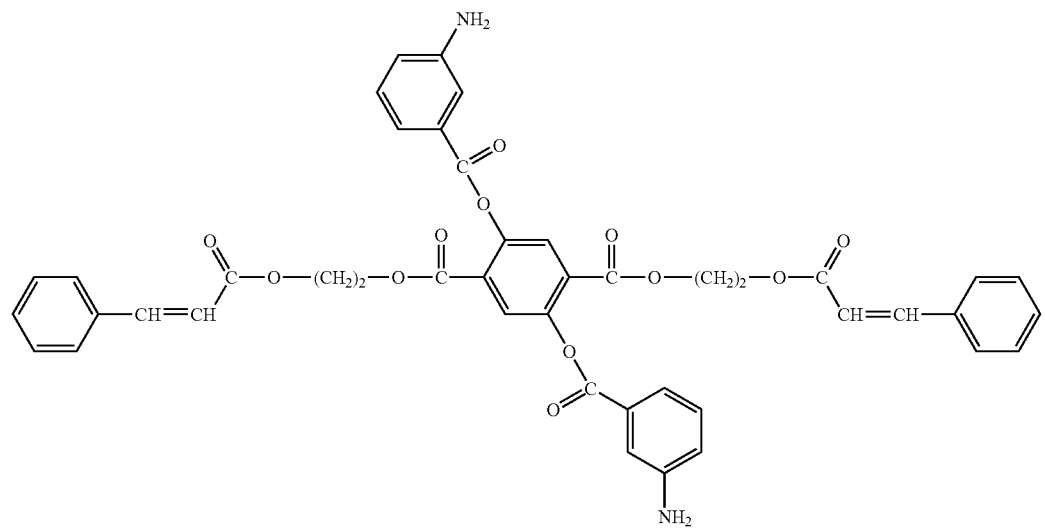

(11)

-continued

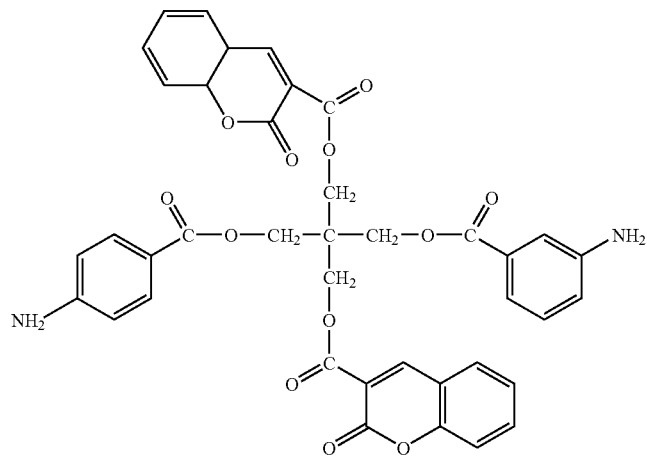
(12)

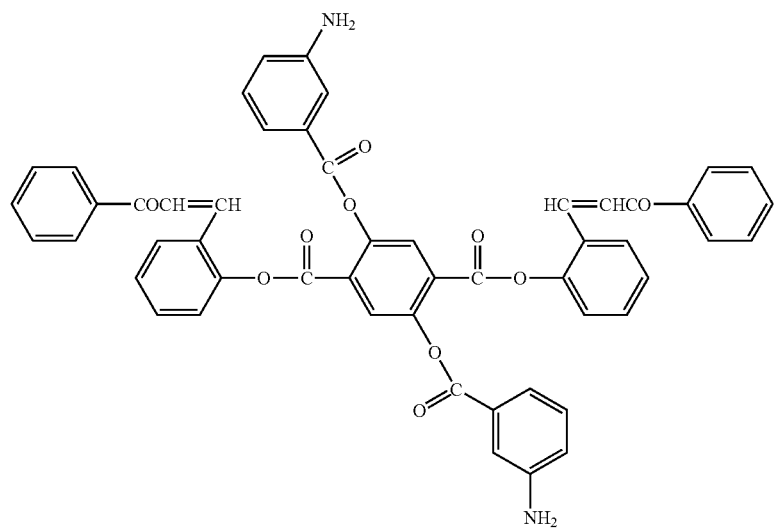
(13)

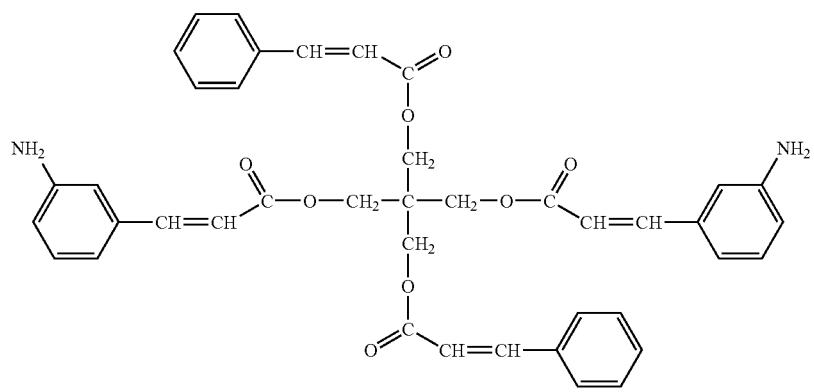
(14)

The diamine of the present invention represented by the general formula (1) can be characterized by a combination of any two of the aforementioned (A-1), (G-1), (Q-1), and (R-1), preferably a combination of three of them, and more preferably a combination of all of them.

Alternatively, the diamine of the present invention represented by the general formula (1) can be characterized by a combination of any two of the aforementioned (A-2), (G2), (Q-2), and (R-2), preferably a combination of three of them, and more preferably a combination of all of them.

Alternatively, the diamine of the present invention represented by the general formula (1) can be characterized by a combination of any two of the aforementioned (A-3), (G3), (Q-3), and (R-3), preferably a combination of three of them, and more preferably a combination of all of them.

Next, a method of sinthesizing the diamine represented by the aforementioned general formula (1) will be hereinafter described.

The diamine represented by the aforementioned general formula (1) wherein M is RCOO— can be synthesized as follows. First, a dinitro compound represented by the general formula (2):

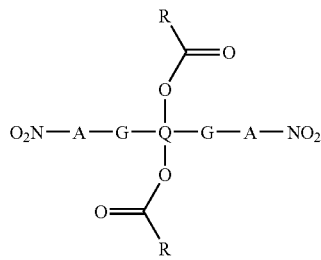

general formula (2)

wherein A, Q, G, and R are as defined in the general formula (1) is produced.

Examples of a specific procedure for synthesizing the dinitro compound include the following synthesizing methods (1-1), (1-2), and (1-3):

Synthesis Method (1-1)

A dihalodihydroxy compound represented by $X'_2$—$(C_nH_{2n-2})$—$(OH)_2$ (wherein $C_nH_{2n-2}$ represents a total number of carbon atoms and hydrogen atoms and is intended to represent neither a distinction between straight- and branch-chain nor an arrangement of a bond of X' C.; n is an integer of 2 to 20; and X' is Cl, Br, or I) is reacted with R—COOH (wherein R is as defined in the general formula (1)) in the presence of a base catalyst such as DBU (diazabicyclo undecene), or the aforementioned dihalodihydroxy compound is reacted with an alkali metal salt such as R—COOCs and R—COOK in an aprotic organic solvent such as dimethylformamide and N-methylpyrrolidone. In this way, $(R—COO)_2$—$(C_nH_{2n-2})$—$(OH)_2$ can be produced.

Then, the produced $(R—COO)_2$—$(C_nH_{2n-2})$—$(OH)_2$ is reacted with $NO_2$—A—COOH (wherein A is as defined in the general formula (1)) in the presence of an esterification catalyst such as toluenesulfonic acid chloride, or it is reacted with $NO_2$—A—COCl. Thus a dinitro compound represented by the general formula (2) wherein G is —COO— is obtained.

Synthesis Method (1-2)

In the same manner as described above, the produced $(R—COO)_2$—$(C_nH_{2n-2})$—$(OH)_2$ is reacted with a halogen compound such as $NO_2$—A—Br, $NO_2$—A—Cl, and $NO_2$—A—I. Thus a dinitro compound corresponding to the general formula (2) wherein G is —O— is obtained.

Synthesis Method (1-3)

$(HOCO)_2$—$(C_nH_{2n-2})$—$(OH)_2$ and R—COCl are reacted to produce an acid anhydride $(RCOOCO)_2$—$(C_nH_{2n-2})$—$(OCOR)_2$ as an intermediate. Then the acid anhydride is hydrolyzed with water to produce $(HOCO)_2$—$(C_nH_{2n-2})$—$(OCO—R)_2$.

The produced $(HOCO)_2$—$(C_nH_{2n-2})$—$(OCO—R)_2$ is reacted with $NO_2$—A—OH in the presence of an esterification catalyst such as toluenesulfonic acid chloride, or it is reacted with $NO_2$—A—OH after conversion of $(HOCO)_2$—$(C_nH_{2n-2})$—$(OCO—R)_2$ into acid chloride $(ClCO)_2$—$(C_nH_{2n-2})$—$(OCO—R)_2$. Thus the dinitro compound corresponding to the general formula (2) wherein G is —OCO— is obtained.

A diamine represented by the general formula (1):

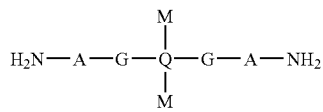

general formula (1)

wherein M is RCOO— is obtained by reduction, for example, by hydrogenation of a nitro group of the thus-obtained dinitro compound.

The aforementioned dinitro compound has double bonds in a reactive group. Under a strict reduction condition, the double bonds are undesirably reduced. Under a strict acidic condition, there is high possibility that ester bonds are decomposed under a strongly acid condition. Furthermore, under an alkaline condition, there is possibility that the Michael addition reaction occurs. For this reason, the reduction condition must be set up adequately.

One of the suitable methods for reducing the aforementioned dinitro compound is hydrogenation in an organic solvent using Pd-carbon black catalyst deactivated by adding a poisoning material, Pt-carbon black catalyst, Pt-activated carbon catalyst, or Pd-activated carbon catalyst whose reactivity is eliminated. The term "Pt-carbon black" is a catalyst having platinum supported on a carrier of carbon black, the term "Pd-carbon black" is a catalyst having palladium supported on a carrier of carbon black, the term "Pd-activated carbon" is a catalyst having palladium supported on a carrier of activated carbon, and the term "Pt-activated carbon" is a catalyst having platinum supported on a carrier of activated carbon.

The Pd-carbon black catalyst to be generally used in hydrogenation has high reactivity, so that an undesired reduction of double bonds may be easily caused. Therefore, it is necessary to use a Pd-carbon black catalyst whose reactivity is deactivated by a poisoning material such as iron and sulfur. The Pt-carbon black catalyst is desirably used in this reduction system, because it gives a higher priority to a reduction of nitro groups than a reduction of double bonds, and produces a desired diamine in high yield. The same result can be obtained using Pt-carbon black catalyst with a poisoning material such as Fe and Na mixed thereinto.

In the Pt-carbon black catalyst, a platinum concentration is about 0.1 to 40% by weight, preferably 1 to 20% by weight. In the Pd-carbon black catalyst and the like, a palladium concentration is about 0.1 to 40% by weight, preferably 1 to 30% by weight. When a concentration of a precious metal is too low, catalyst does not work well. Although a reaction rate tends to increase with the concentration of a precious metal, too much higher concentration decreases catalytic effects. Both Pt-carbon black and Pd-carbon black can catalyze effectively in the dry state or in the water-absorbed. Industrially, the water-absorbed state is preferable for preventing dust from rising and for easy handling.

In general, a nitro group is reduced using a catalyst having a precious mental supported on a carrier of an activated carbon. However, when the nitro group is reduced, the catalyst having activate carbon as a carrier causes an undesired reduction of double bonds at a higher rate than a catalyst having carbon black as a carrier. Therefore, it is preferable to use a precious metal catalyst having carbon black as a carrier. However, even in the case of using a catalyst having precious metal supported on activated carbon, a reduction of double bonds of reactive groups can be curbed and nitro groups can be preferentially reduced by blending a larger amount of poisoning substances into the catalyst than a catalyst having carbon black as a carrier. For example, a catalyst made by blending Fe and Na with a catalyst having platinum supported on activated carbon exhibits the same reduction selectivity to nitro groups as Pt-carbon black. Therefore, this catalyst can be preferably used for the aforementioned hydrogenation.

An organic solvent used for the aforementioned reduction does not inhibit the reduction reaction and may be any solvent which can dissolve diamine and dinitro compound. Examples of organic solvents include: alcohols; ethers such as dioxane; aromatic solvents such as toluene and xylene; sulfoxide solvents such as dimethyl sulfoxide and diethyl sulfoxide; formamide solvents such as N,N-dimethylformamide and N,N-diethylformamide; acetamide solvents such as N,N-dimethylacetamide and diethylacetamide; pyrrolidone solvents such as N-methyl-2-pyrrolidone and N-vinyl-2-pyrrolidone; phenol solvents such as phenol, o-cresol, m-cresol, p-cresol, xylenol, phenol halide, and catechol; hexamethylphosphoramide; and y-butyrolactone.

Another suitable method for reducing the aforementioned dinitro compound is the Bechamp reduction. The Bechamp reduction is carried out by adding the aforementioned dinitro compound and Fe powder to a solvent and heating the solvent at a temperature of 130° C. or less. Any solvents including the aforementioned solvents can be used. Preferable solvents are acetic acid, alcohol, dioxane, or the like.

Thus, the method for synthesizing the diamine represented by the general formula (1) wherein M is RCOO— by reducing a dinitro compound has been described above. The diamine represented by the general formula (1) wherein M is RCOO— can also be synthesized by adding a reactive group to intermediate diamine. Examples of such synthesis method (21) and (2-2) will be hereinafter described.

Synthesis Method (2-1)

A dihalodihydroxy compound $(X')_2$—$(C_nH_{2n-2})$—$(OH)_2$ (wherein n is an integer of 2 to 20) is reacted with $NO_2$—A—COOH (wherein A is as defined in the general formula (1)) in the presence of an esterification catalyst such as toluenesulfonic acid chloride or with $NO_2$—A—COCl to produce a dinitro compound $(NO_2$—A—$COO)_2$—$(C_nH_{2n-2})$—$(X')_2$. This dinitro compound is reduced to produce a diamine compound $(NH_2$—A—$COO)_2$—$(C_nH_{2n-2})$—$(X')_2$. Then this diamine compound is reacted with R—COOH (wherein R is the same as defined in the general formula (1)) in the presence of a basic catalyst such as DBU or with an alkali metal salt such as R—COOCs and R—COOK in an aprotic organic solvent such as dimethylformamide and N-methylpyrrolidone. Thus $(NH_2$—A—$COO)_2$—$(C_nH_{2n-2})$—$(OCO$—$R)_2$ is obtained.

Synthesis Method (2-2)

The aforementioned dihalodihydroxy compound is reacted with a halide such as $NO_2$—A—Br, $NO_2$—A—Cl, and $NO_2$—A—I to produce a dinitro compound $(NO_2$—A—$O)_2$—$(C_nH_{2n-2})$—$(X')_2$. This dinitro compound is reduced to produce $(NH_2$—A—$O)_2$—$(C_nH_{2n-2})$—$(X')_2$. In the same manner as the aforementioned synthesis method (2-1), $(NH_2$—A—$O)_2$—$(C_nH_{2n-2})$—$(X')_2$ is then reacted with R-COOCs or R—COOH. Thus $(NH_2$—A—$O)_2$—$(C_nH_{2n-2})$—$(OCO$—$R)_2$ is obtained.

Further, the diamine represented by the general formula (1) wherein M is RCOO— can also be synthesized by adding a reactive group and subsequently introducing amine group. An Example of such synthesis method (3-1) will be hereinafter described.

Synthesis Method (3-1)

An alkali metal salt such as $NH_2$—A—COOCs and $NH_2$—A—COOK is reacted with $(X')_2$—$(C_nH_{2n-2})$—$(OCO$—$R)_2$ in an aprotic solvent. Thus $(NH_2$—A—$COO)_2$—$(C_nH_{2n-2})$—$(OCO$—$R)_2$ is obtained.

The diamine represented by the general formula (1) wherein G is —NH—, —NHCO—, or —CONH— can be synthesized, for example, in following synthesis process (a), (b), and (C), respectively.

Synthesis Method (a) in the Case where G is —NH—:

An alkali metal salt such as RCOOCa and RCOOK is reacted with $Br_2$—$(C_nH_{2n-2})$—$(NH_2)_2$ or the like in an organic polar solvent to produce a diamino compound (R—$COO)_2$—$(C_nH_{2n-2})$—$(NH_2)_2$. Then this diamino compound is reacted with a halide such as $NO_2$—A—Br, $NO_2$—A—Cl, and $NO_2$—A—I to produce a dinitro compound (R—$COO)_2$—$(C_nH_{2n-2})$—$(NH$—A—$NO_2)_2$. An $NO_2$ group of this dinitro compound is reduced. Thus the diamine represented by the general formula (1) wherein G is —NH— is obtained.

Synthesis Method (b), in the Case where G is —NHCO—

(R—$COO)_2$—$(C_NH_{2n-2})$—$(COCL)_2$ is reacted with $H_2N$—A—$NH_2$. Thus the diamine compound represented by the general formula (1) wherein G is —NHCO— is obtained. Alternatively, (R—$COO)_2$—$(C_nH_{2n-2})$—$(COCl)_2$ is reacted with $H_2N$—A—$NO_2$ to produce a dinitro compound (R—$COO)_2$—$(C_nH_{2n-2})$—$(CONH$—A—$NO_2)_2$. An $NO_2$ group of the dinitro compound is reduced. Thus the diamine represented by the general formula (1) wherein G is —NHCO— is obtained.

Synthesis Method (c) in the Case where G is —CONH—:

An alkali metal salt such as RCOOCa and RCOOK is reacted with $Br_2$—$(C_nH_{2n-2})$—$(NH_2)_2$ or the like in an organic polar solvent to produce a diamine compound (R—$COO)_2$—$(C_nH_{2n-2})$—$(NH_2)_2$. Then this diamino compound is reacted with $NO_2$—A—CO—Cl to produce a dinitro compound (R—$COO)_2$—$(C_nH_{2n-2})$—$(NHCO$—A—$NO_2)_2$. An $NO_2$ group of this dinitro compound is reduced. Thus the diamine represented by the general formula (1) wherein G is —CONH— is obtained.

Next, a method of synthesizing a diamine represented by the general formula (1) wherein M is ROCO— will be hereinafter described. For example, such diamine can be produced using a following procedure (4-1).

Procedure (4-1)

Z—COCl or Z—COOH (wherein Z is a reactive group included in the R group in the general formula (1 is reacted with X'—$(C_mH_{2m})$—OH (wherein X' is halogen and m is an integer of 2 to 20) in the presence of an ester condensing agent to produce Z—COO—$(C_mH_{2m})$—X' (wherein Z—COO—$(C_mH_{2m})$— corresponds to R in the general formula (1)).

Next, Z—COO—$(C_mH_{2m})$—X' is reacted with an alkali metal salt such as $(HO)_2$—$(C_nH_{2n-2})$—$(COOCS)_2$ and $(HO)_2$—$(C_nH_{2n-2})(COOK)_2$ (wherein Q is as defined in the general formula (1)) to produce $\{Z$—COO—$(C_mH_{2m})$—$OCO\}_2$—$(C_nH_{2n-2})$—$(OH)_2$. This $\{Z$—COO—$(C_mH_{2m})$—$OCO\}_2$—$(C_nH_{2n-2})$—$(OH)_2$ is reacted with $NO_2$—A—X' or $NO_2$—A—COCl (wherein A is as defined in the general formula (1) and X'is halogen) to produce {Z—COO—(C$_m$H$_{2n-2}$)—OCO}$_2$—(C$_n$H$_{2n-2}$)—(O—A—NO$_2$)$_2$ or {Z—COO—(C$_m$H$_{2m}$)—OCO}$_2$—(C$_n$H$_{2n-2}$)—(OCO—A—NO$_2$)$_2$. Then {Z—COO—(C$_m$H$_{2m}$)—OCO}$_2$—(C$_n$H$_{2n-2}$)—(O—A—NO$_2$)$_2$ or {Z—COO—(C$_m$H$_{2m}$)—OCO}$_2$—(C$_n$H$_{2n-2}$)—(OCO—A—NO$_2$)$_2$ is reduced under the same condition as the case of the dinitro compound produced in the course of synthesizing the diamine represented by the general formula (1) where M is RCOO—. Thus the diamine represented by the general formula (1) wherein M is ROCO— is produced.

In the above syntheses, the case where Q is (C$_n$H$_{2n-2}$) has been described. In the like manner, the desired diamine can be produced, even when Q is other organic group. However, in the reaction in which the aforementioned alkali metal salt such as RCOOCa and RCOOK is used, the aforementioned X' must be bonded on an aliphatic carbon. It should be understood by those skilled in the art that variations and improvements of the synthesizing method may be made in accordance with a structure of an organic group.

Another embodiment of the novel diamine according to the present invention is represented by the general formula (3):

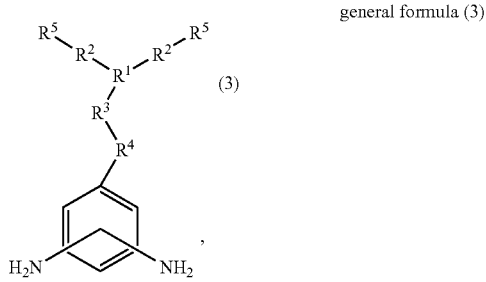

general formula (3)

wherein $R^2$, $R^3$, and $R^4$ are a divalent organic group, $R^1$ is a divalent organic group, m is an integer of 1 or more, and n is an integer of 0 or more. $R^5$ represents a monovalent organic group having a reactive group derived from cinnamic acid, chalcone, benzalacetophenone, stilbene, coumarin, pyrone, allyl, propargyl, and acetylene. The cinnamic acid, chalcone, benzalacetophenone, stilbene, coumarin, pyrone, allyl, propargyl, and acetylene have both photoreactivity and thermoreactivity and can be used in various cases.

Specifically, $R^5$ is a monovalent organic group having a reactive group selected from the following group (II) consisting of

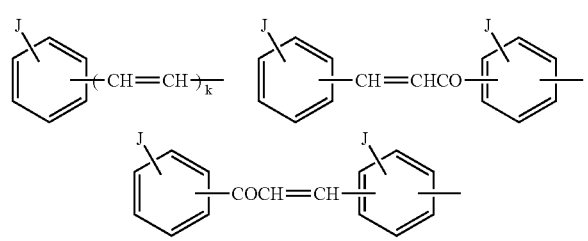

Group (II)

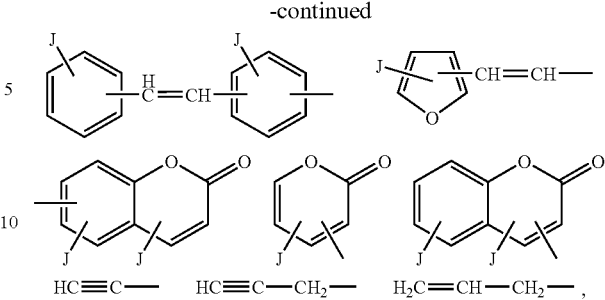

-continued wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof. Preferably, J is a methyl group, methoxy group, or halogen.

In the general formula (3), $R^1$ is preferably $C_nH_{2n-1}$ (wherein n is an integer of 1 to 20), a benzene ring, or a naphthalene ring.

In the general formula (3), $R^2$ is a single bond, —COO—, —NHCO—, —(C$_m$H$_{2m}$)COO—, or —OCO(C$_m$H$_{2m}$)COO— (wherein m is an integer of 2 to 20).

In the general formula (3), $R^3$ is a single bond or —COO—, and $R^4$ is a single bond, —CH$_2$—, or —COO—.

The diamine represented by the general formula (3) according to the present invention is synthesized as follows. The first step is to synthesize a compound represented by the general formula (4) in which a nitro group is bonded instead an amino group of the general formula (3)

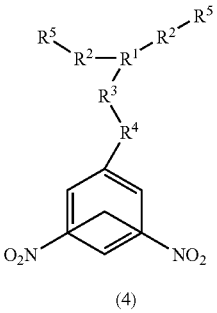

general formula (4)

(wherein $R^2$, $R^3$, and $R^4$ are a divalent organic group, $R^1$ is a trivalent organic group, $R^5$ is a monovalent organic group having a reactive group derived from cinnamic acid, chalcone, benzalacetophenone, stilbene, coumarin, pyrone, allyl, propargyl, and acetylene. Then, the diamine represented by the general formula (4) is reduced. Thus the diamine represented by the general formula (3) is produced).

For example, C$_6$H$_5$CH=CHCOOH is selected from the group (V) of carboxylic acids having a reactive group represented by the group (V) of the derivatives of cinnamic acid:

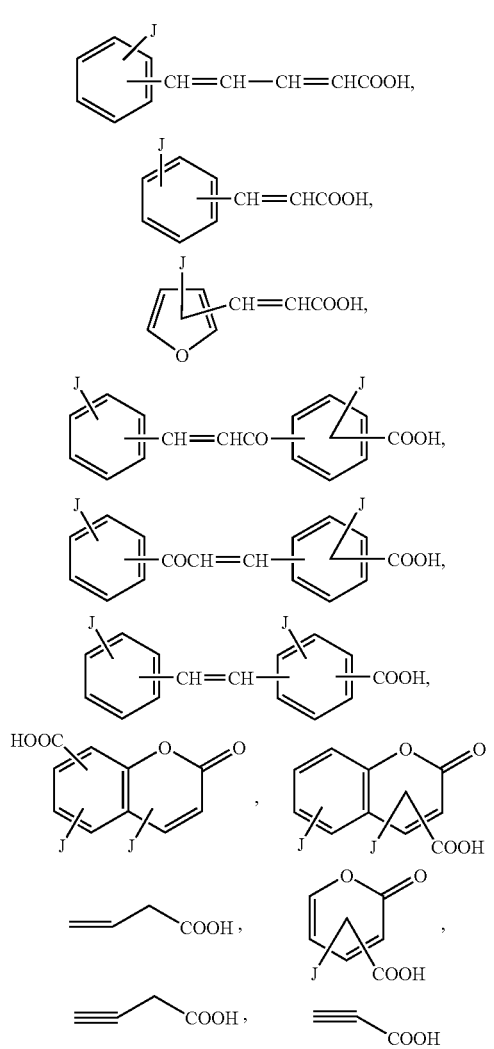

(V)

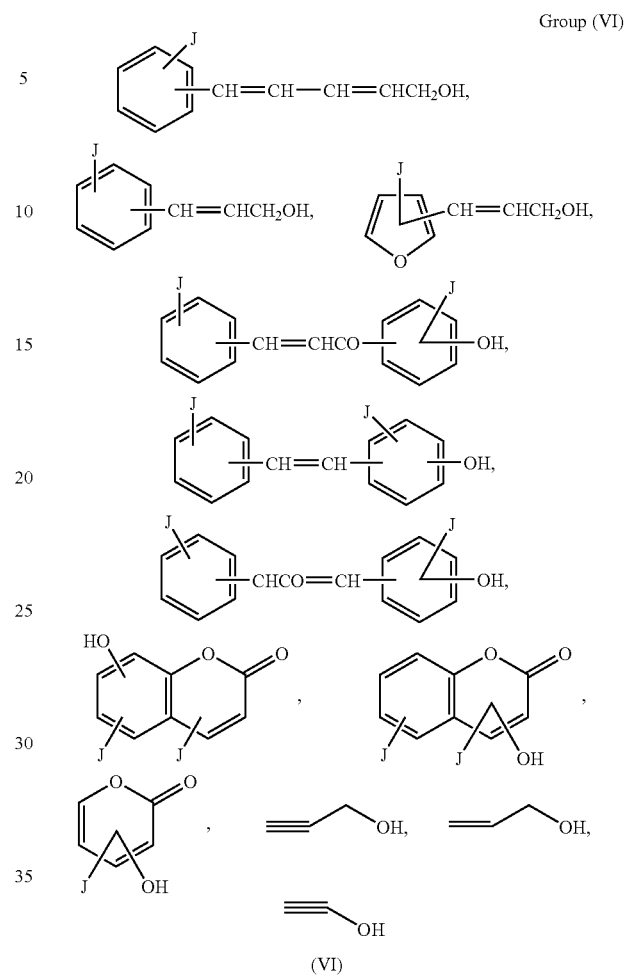

Group (VI)

(VI)

(wherein J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof, and wherein J is preferably a methyl group, methoxy group, or halogen. An alkali metal salt, e.g., Cs salt, K salt, or Na salt of the $C_6H_5CH=CHCOOH$ is reacted with $X-C_nH_{2n-1}(OH)-X$ (wherein n is an integer of 1 to 20 and X represents halogen) in an organic polar solvent to produce $(C_6H_5CH=CHCOO)_2C_nH_{2n-1}(OH)$. Then this $(C_6H_5CH=CHCOO)_2C_nH_{2n-1}(OH)$ is reacted with dinitrobenzoyl chloride or dinitrobenzoic acid in the presence of an esterification catalyst. Thus $(C_6H_5CH=CHCOO)_2C_nH_{2n-1}OCOC_6H_3(NO_2)_2$ can be obtained. In the general formula (4), $R^2$ is —, $R^1$ is $C_nH_{2n-1}$, $R^3$ is a single bond, and $R^4$ is COO. When another carboxylic acid having a photosensitive group of the aforementioned group (V) is selected instead of $C_6H_5CH=CHCOO$, the similar processes of reaction can be applied.

For another example, hydroxychalcone is selected from the group (VI) of compounds having a photosensitive group and hydroxyl group represented by the group (VI) (wherein J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof, and wherein J is preferably a methyl group, methoxy group, or halogen), and is reacted with $X(C_mH_{2m})COCl$ (wherein m is an integer of 2 to 20 and X represents halogen) to produce $C_6H_5CH=CHCOC_6H_4OCO(C_mH_{2m})-X$. Then this is reacted with an alkali metal salt of a compound such as dicarboxyphenol, which has two carboxy groups and one hydroxy group, in an organic polar solvent to produce $\{C_6H_5CH=CHCOC_6H_4OCO(C_mH_{2m})-OCO\}_2-C_6H_3(OH)$. This is reacted with dinitrobenzoyl chloride or dinitrobenzoic acid in the presence of an esterification catalyst. Thus $\{C_6H_5CH=CHCOC_6H_4OCO\ (C_mH_{2m})-OCO\}_2-C_6H_3OCOC_6H_3\ (NO_2)_2$ can be obtained. In the general formula (4), $R^2$ is $OCO(C_mH_{2m})-OCO$, $R^1$ is $C_6H_3$, $R^3$ is a single bond, and $R^4$ is COO. Where another carboxylic acid having a photosensitive group and hydroxy group represented by the aforementioned group (VI) is selected, the same result can be achieved.

For still another example, $C_6H_5CH=CHCOOH$ is selected from the group (V) of carboxylic acids having a photosensitive group represented by the group (V) of derivatives of cinnamic acid

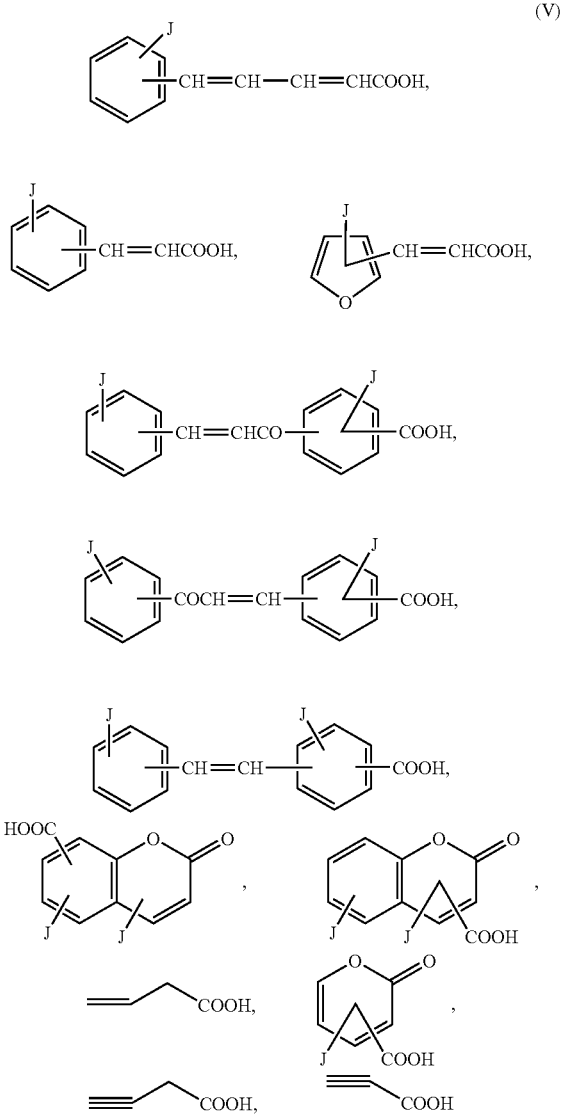

(wherein J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof, and wherein J is preferably a methyl group, methoxy group, or halogen). This acid chloride is reacted with X—$(C_mH_{2m})$—OH (wherein m is an integer of 2 to 20 and X represents halogen) to produce $C_6H_5CH$=$CHCOO$— $(C_mH_{2m})$—X. Then this is reacted with an alkali metal salt of a compound which has two carboxy groups and one hydroxy group, e.g., dicarboxyphenol, in an organic polar solvent to produce $\{C_6H_5CH$=$CHCOO$—$(C_mH_{2m})$—$OCO\}_2$—$C_6H_3(OH)$. Then this is reacted with dinitrobenzoyl chloride or dinitrobenzoic acid in the presence of an esterification catalyst. Thus $\{C_6H_5CH$=$CHCOO$— $(C_mH_{2m})$—$OCO\}_2$—$C_6H_3OCOC_6H_3(NO_2)_2$ can be produced. In the general formula (4), $R^2$ is —$(C_mH_{2m})$—OCO, $R^1$ is $C_6H_3$, $R^3$ is a single bond, and $R^4$ is COO. When another carboxylic acid having a photosensitive group represented by the aforementioned group (V) is selected, the similar processes of reaction can be applied.

For another example, $C_6H_5CH$=$CHCOOH$ is selected from the group (V) of carboxylic acid and the like having a photosensitive group represented by the group (V) of derivatives of cinnamic acid, and is reacted with a compound such as dihydroxybenzoic acid having one carboxy group and two hydroxy groups to produce $(C_6H_5CH$=$CHCOO)_2$—$C_6H_3$—COOH. Then this is reacted with thionyl chloride to produce acid chloride or with dinitrobenzil alcohol in the presence of an esterification catalyst to produce $(C_6H_5CH$=$CHCOO)_2$—$C_6H_3COOCH_2C_6H_3(NO_2)_2$. In the general formula (4), $R^2$ is a single bond, $R^1$ is $C_6H_3$, $R^3$ is COO, and $R^4$ is $CH_2$. Where another carboxylic acid having a photosensitive group represented by the aforementioned group (V) is selected, the same result can be achieved.

These dinitro compounds are reduced by Bechamp reduction or hydrogenerated using Pd-carbon black catalyst or Pt-carbon black catalyst which is inactivated by adding a poisoning material such as iron and sulfur. Thus the diamine compound represented by the general formula (3) is obtaind.

General formula (3)

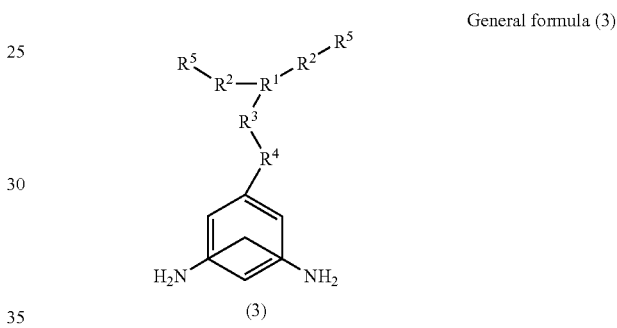

(3)

The method of reducing a nitro group, catalyst, and solvent are the same as used for producing the diamine represented by the general formula (1).

While the method of synthesizing a diamine by reducing a dinitro compound having a reactive group has been described above, the diamine represented by the general formula (3) can be produced by bonding a reactive group to any diamine.

An example of a method of bonding a reactive group to a diamine will be hereinafter described.

For example, a compound such as hydroxy terephthalic acid having a hydroxy group and two carboxy groups is reacted with dinitrobenzoyl chloride to produce $(NO_2)_2C_6H_3COOC$—$_6H_3(COOH)_2$. Then this $(NO_2)_2C_6H_3COO$—$C_6H_3(COOH)_2$ is reduced and reacted to produce an alkali metal salt. The alkali salt is reacted with alkyl halide, for example, $Br(CH_2)_nOCOCH$=$CHC_6H_5$ to produce $(NH_2)_2C_6H_3COO$—$C_6H_3[COO(CH_2)_nOCOCH$=$CHC_6H_5]2$. Thus, a diamine having photoreactivity and thermoreactivity can be produced.

Next, a novel acid dianhydride according to the preset invention will be hereinafter described.

A novel acid anhydride of the present invention is used for producing a novel polyimide having a reactive group derived from cinnamic acid, chalcone, benzalacetophenone, stilbene, coumarin, pyrone, allyl, propargyl, and acetylene skeleton on its dianhydride residue, and the acid anhydride has these reactive groups on its side chain.

The acid dianhydride of the present invention is represented by the general formula (5)

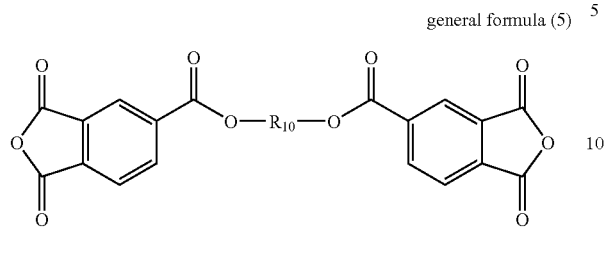

general formula (5)

(wherein $R^{10}$ represents a divalent organic group including a reactive group selected from the derivatives of cinnamic acid, chalcone, benzalacetophenone, stilbene, coumarin, pyrone, allyl, propargyl, and acetylene).

In the general formula (5) representing the acid dianhydride, $R^{10}$ is preferably a divalent organic group selected from the following group (VII):

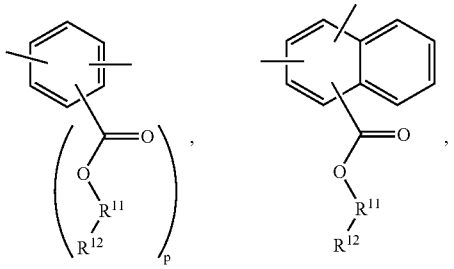

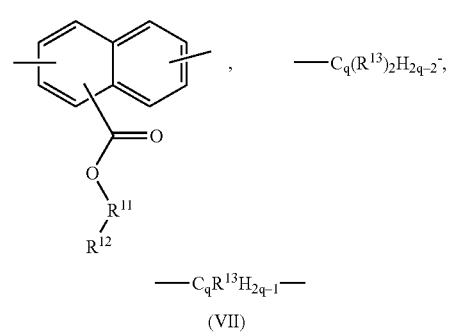

(wherein $R^{11}$ is a single bond, $-C_rH_{2r}OOC-$, or $-C_rH_{2r}COO-$, $R^{12}$ and $R^{13}$ each are a monovalent organic group derived from cinnamic acid, chalcone, benzalacetophenone, stilbene, coumarin, pyrone, allyl, propargyl, and acetylene, q is an integer of 1 to 20, and p is 1 or 2, and an ester bond is on the side of $R^{12}$ when $R^{11}$ is $-C_rH_{2r}OC-$, or $-C_rH_{2r}COO-$).

In the general formula (5) representing the acid dianhydride, $R^{11}$ has a structure derived from cinnamic acid, chalcone, benzalacetophenone, stilbene, coumarin, pyrone, allyl, propargyl, and acetylene, and preferably a monovalent organic group having a reactive group selected from the group (II) consisting of:

Group (II)

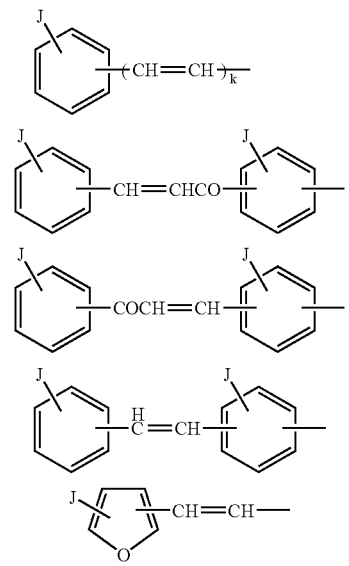

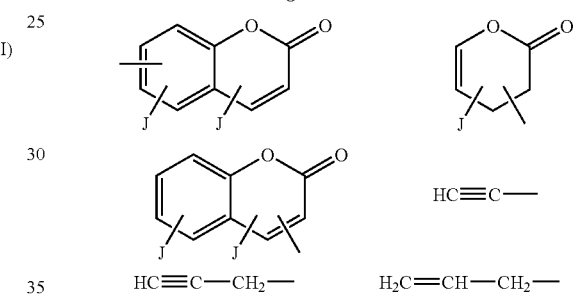

(wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof).

In the aforementioned group (VII), $R^{13}$ is preferably a monovalent organic group selected from the following group (VIII) consisting of Group (VIII)

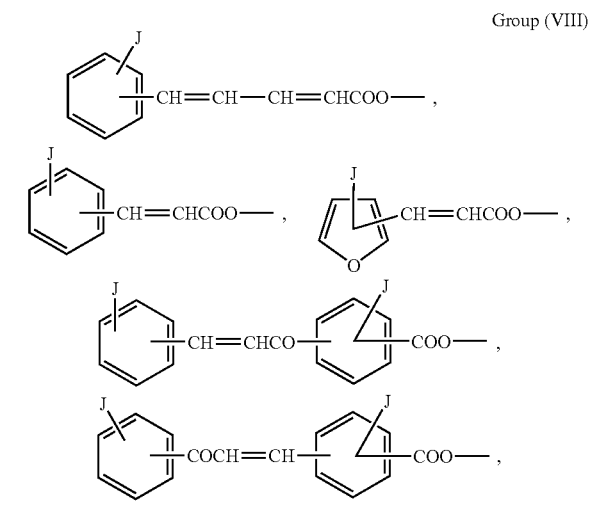

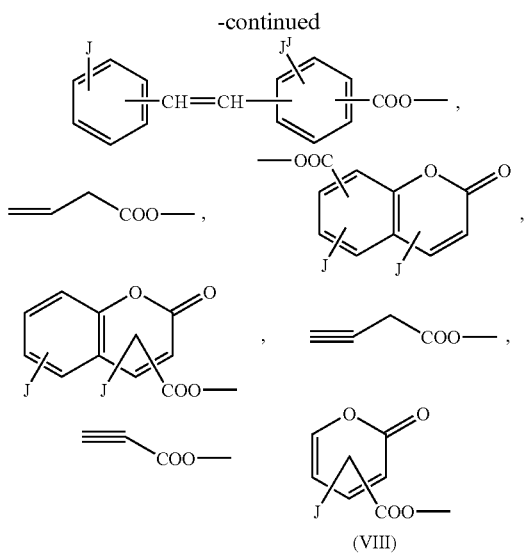

(VIII)

(wherein J represents a group capable of arbitrarily substituting for hydrogen atom of an aromatic ring and independently represents halogen, C1 to C3 alkyl, C1 to C3 alkoxy, or C1 to C3 fluoroalkyl, or a combination thereof and is preferably a methyl group, methoxy group, or halogen).

Next, a novel acid dianhydride represented by the general formula (5)

General formula (5)

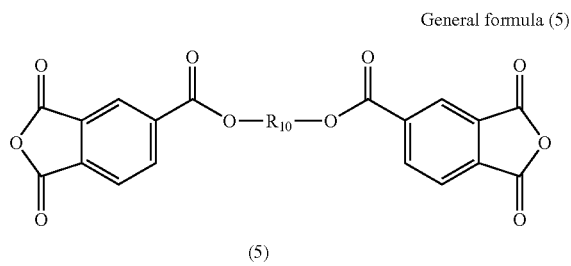

(5)

will be described.

The acid dianhydride of the present invention can be produced by reacting a dihydroxy compound derived from cinnamic acid, chalcone, benzalacetophenone, stilbene, coumarin, pyrone, allyl, propargyl, and acetylene with trimellitic anhydride chloride or trimellitic anhydride in the presence of an esterification catalyst.

The dihydroxy compound derived from cinnamic acid, chalcone, benzalacetophenone, stilbene, coumarin, pyrone, allyl, propargyl, and acetylene is synthesized as follows.

In the case of a reactive group having a carboxy group (derived from cinnamic acid, chalcone, benzalacetophenone, stilbene, coumarin, pyrone, allyl, propargyl, and acetylene), $X-(C_sH_{2s})-OH$ (wherein x is halogen and s is an integer of 1 to 20) is reacted with $R^6$—COOH or $R^6$—COCl (wherein $R^6$ is a monovalent organic group derived from cinnamic acid, chalcone, benzalacetophenone, stilbene, coumarin, pyrone, allyl, propargyl, and acetylene) to produce $X-(C_sH_{2s})-OOC-R^6$.

$X-(C_sH_{2s})-OOC-R^6$ is reacted with an alkali metal salt of $(HO)_2-C_6H_3(COOH)$ or with $-C_6H_3(COOH)-$ in the presence of a strong base such as diazabicycloundecene to produce $(HO)_2-C_6H_3\{COO-(C_sH_{2s})-OOC-R^6\}$.

Likewise, $X-(C_sH_{2s})-OOC-R^6$ is reacted with $(HO)_2-C_6H_2-(COOH)_2$, $(HO)_2-C_6H_2(COOH)$ or $(HO)_2-C_{10}H_5(COOH)$ (wherein $C_{10}H_5$ represents a naphthalene ring) to produce $(HO)_2-C_6H_2\{COO-(C_sH_{2s})-OOC-R^6\}_2$, $(HO)_2-C_6H_2\{COO-(C_sH_{2s})-OOC-R^6\}$, or $(HO)_2-C_{10}H_5\{COO-(C_sH_{2s})-OOC-R^6\}$.

In the case of a reactive group having a hydroxy group (derived from cinnamic acid, chalcone, benzalacetophenone, stilbene, coumarin, pyrone, allyl, propargyl, and acetylene), $X-(C_sH_{2s})-COOH$ (wherein X is halogen and s is an integer of 1 to 20) is reacted with $R^6$—OH in the presence of an ester catalyst or $R^6-(C_sH_{2s})-COCl$ is reacted with $R^6$—OH (wherein $R^6$ is a monovalent organic group derived from cinnamic acid, chalcone, benzalacetophenone, stilbene, coumarin, pyrone, allyl, propargyl, and acetylene) to produce $X-(C_sH_{2s})-COO-R^6$.

$X-(C_sH_{2s})-COO-R^6$ is reacted with an alkali metal salt of $(HO)_2-C_6H_3(COOH)$ or with $-C_6H_3(COOH)-$ in the presence of a strong base such as diazabicycloundecene to produce $(HO)_2-C_6H_3\{COO-(C_sH_{2s})-COO-R^6\}$.

Likewise, $X-(C_sH_{2s})-COO-R^6$ is reacted with $(HO)_2-C_6H_2(COOH)_2$, $(HO)_2-C_6H_2(COOH)$ or $(HO)_2-C_{10}H_5(COOH)$ (wherein $C_{10}H_5$ represents a naphthalene ring) to produce $(HO)_2-C_6H_2\{COO-(C_sH_{2s})-COO-R^6\}_2$, $(HO)_2-C_6H_2\{COO-(C_sH_2s)-COO-R^6\}$, or $(HO)_2-C_{10}H_5\{COO-(C_sH_{2s})-COO-R^6\}$.

Alternatively, $(HO)_2-C_qH_{2q-2}(X)_2$ or $(HO)_2-C_qH_{2q-1}(X)$ (wherein q is an integer of 1 to 20 and X represents halogen) is reacted with an alkali metal salt of HOOC—$R^6$ (wherein $R^6$ is a monovalent organic group derived from cinnamic acid, chalcone, benzalacetophenone, stilbene, coumarin, pyrone, allyl, propargyl, and acetylene) or reacted with HOOC—$R^6$ in the presence of a strong base such as diazabicycloundecene to produce $(HO)_2-C_qH_{2q-2}(OOC-R^6)_2$ or $(HO)_2-C_qH_{2q-1}(OOC-R^6)$.

The desired acid dianhydride can be produced by reacting dihydroxy compounds including cinnamic acid, chalcone, benzalacetophenone, stilbene, coumarin, pyrone, propargyl, and acetylene with trimellitic anhydride chloride or trimellitic anhydride in the presence of an esterification catalyst.

The thus-obtained novel acid dianhydride represented by the general formula (5) is a novel acid dianhydride having cinnamic acid, chalcone, benzalacetophenone, stilbene, coumarin, pyrone, allyl, propargyl, and acetylene on a side chain thereof. Moreover, it is useful as a monomer of a novel polyimide composition having both photoreactivity and thermoreactivity specific to the derivatives of cinnamic acid.

Next, a polyimide composition of the present invention containing the aforementioned novel diamine and/or novel acid dianhydride according to the present invention will be hereinafter described.

A novel polyimide composition according to the present invention is produced by reaction of the novel diamine characterized by having a reactive group derived from cinnamic acid, chalcone, benzalacetophenone, stilbene, coumarin, pyrone, allyl, propargyl, and acetylene and the acid dianhydride having a reactive group derived from cinnamic acid, chalcone, benzalacetophenone, stilbene, coumarin, pyrone, allyl, propargyl, and acetylene, and has both photoreactivity and thermoreactivity specific to the reactive group.

An embodiment of a novel polyimide composition according to the present invention will be described citing a specific structure. However, a structure of the novel polyimide composition is not particularly limited as far as a diamine residue and/or acid anhydride residue has a group derived from cinnamic acid, chalcone, benzalacetophenone, stilbene, coumarin, pyrone, allyl, propargyl, and acetylene.

A novel polyimide composition according to the present invention has repeating units represented by the general formula (A):

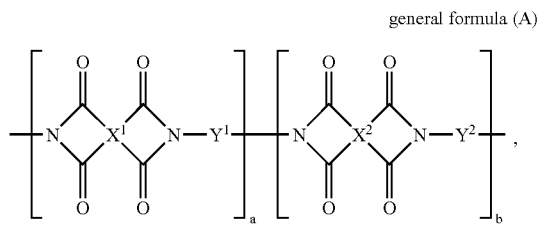

general formula (A)

wherein $X^1$ and $X^2$ represents a tetravalent organic group and $Y^1$ or $Y^2$ represent a divalent organic group. At least one of organic groups may be derived from the novel diamine represented by the general formulas (1) or (3) or the novel acid dianhydride represented by the general formula (5). Preferably, two or more of the residues $X^1$, $X^2$, $Y^1$, and $Y^2$, as the residues of the novel diamine and novel acid dianhydride having photoreactivity and thermoreactivity, are included in a polymer molecular.

In a preferable embodiment of a polyimide according to the present invention, $Y^1$ represents a residue of the diamine according to the present invention having a structure represented by the general formula (1) or (3). In this case, it is preferable that "a" represents an integer of 1 or more, "b" represents an integer of 0 or more, and a/(a+b) is 0.01 or more, so that the produced polyimide exhibits photoreactivity and thermoreactivity. The a/(a+b) is preferably 0.01 to 1, more preferably 0.1 to 1, and most preferably 0.2 to 1. In this case, a and b each represents the number of an imide unit in the polyimide, and a/(a+b) represents a ratio of an imide unit having Y1.

Specifically, where $Y^1$ is derived from the novel diamine represented by the general formula (1) or (3), the polyimide preferably contains 1 wt % or more of repeating units represented by the general formula (B):

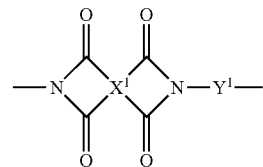

general formual (B)

(wherein $X^1$ is a tetravalent organic group and $Y^1$ represents a diamine residue represented by the aforementioned general formula (1) or (3)).

In this case, it is preferred that $X^1$ and $X^2$ are a tetravalent organic group having 1 to 3 aromatic groups or aliphatic groups.

The polyimide composition according to the present invention may have any structure as far as an acid dianhydride residue is derived from cinnamic acid, chalcone, benzalacetophenone, stilbene, coumarin, pyrone, allyl, propargyl, and acetylene. Examples of the polyimide composition may include the one represented by the following general formula (C):

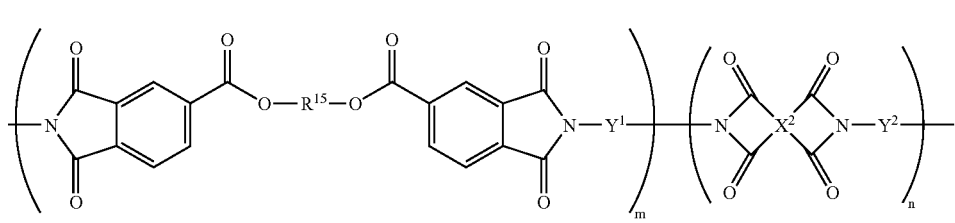

general formula (C)

(wherein $R^{15}$ is a divalent organic group containing a reactive group derived from cinnamic acid, chalcone, benzalacetophenone, stilbene, coumarin, pyrone, allyl, propargyl, and acetylene, $Y^1$ and $Y^2$ each are a divalent organic group, $X^2$ is a tetravalent organic group, m is an integer of one or more, and n is an integer of 0 or more).

In the general formula (C), $R^{15}$ is preferably a divalent organic group selected from the following group (VII)

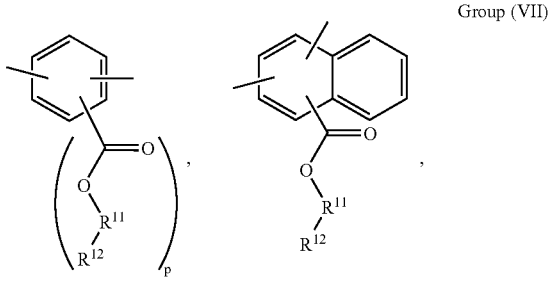

Group (VII)

-continued

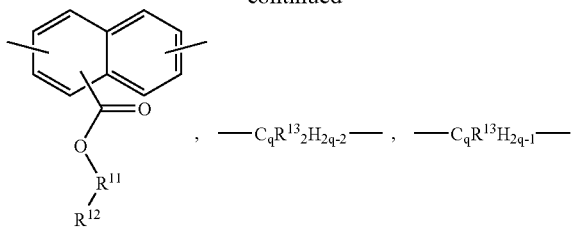

(wherein $R^{11}$ represents a single bond, —$C_rH_{2r}$OOC—, or —$C_rH_{2r}$COO—, $R^{12}$ and $R^{13}$ represent a group derived from cinnamic acid, chalcone, benzalacetophenone, stilbene, coumarin, pyrone, allyl, propargyl, and acetylene, q and r are an integer of 1 to 20, p is 1 or 2, and ester bond is on the $R^{12}$ side when $R^{11}$ is —$C_rH_{2r}$OOC— or —$C_rH_{2r}$COO—).

A polyimide composition to be synthesized from the diamine represented by the general formula (1) or (3) according to the present invention will be described.

First, the diamine represented by the general formula (1) or (3) is reacted with an acid anhydride in an organic polar solvent to form a polyamide acid. In general, polyamide acid can be obtained by reacting diamine with acid anhydride in an organic solvent as follows.

In an inert atmosphere such as argon and nitrogen, a diamine represented by the general formula (D):

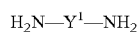          (D)

(wherein $Y^1$ is a diamine residue represented by the general formula (1) or (3)) and acid anhydride represented by the general formula (E):

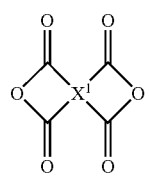          (E)

(wherein $X^1$ is a residue of an acid dianhydride residue represented by the general formula (5) or of another acid anhydride) are dissolved or diffused in an organic solvent to react them with each other. When the diamine and acid dianhydride are substantially equimolar in the number of moles, polyamide acid solution having repeating units represented by the general formula (F):

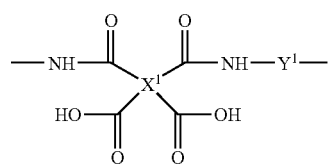          (F)

is formed. When excessive moles of acid anhydride is used in comparison with the amount of diamine, a diamine compound represented by the general formula (G):

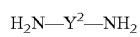          (G)

(wherein $Y^2$ is a diamine residue represented by the general formula (1) or (3)) is dissolved in an organic solvent or diffused in a slurry state or in a solid state and then added to the aforementioned polyamide acid solution. After that, acid dianhydride represented by the general formula (D) or a general formula (H):

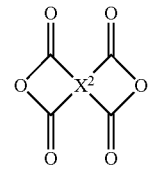          (H)

(wherein $X^2$ is a residue of the acid dianhydride represented by the general formula (5) or another acid dianhydride) is added to the above-obtained solution to obtain a polyamide acid copolymer solution having repeating units represented by the following general formula (I):

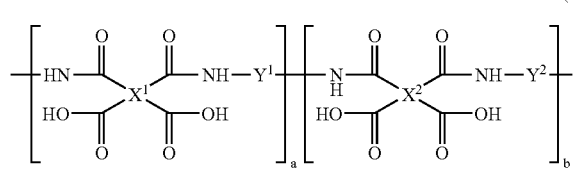          (I)

(wherein c and d each are any integer). Thus, any polyamide acid copolymer solution (namely, c and d in the general formula (I) each are any integer) can be obtained by controlling the mole ratio of acid dianhydride component to diamine component. Alternatively, a polyamide acid copolymer can be obtained in which the bonding order of acid dianhydride residues and diamine residues is arbitrarily controlled by adjusting the adding order of acid dianhydride component and diamine component.

The adding order of monomers is as follows. First, compounds represented by the aforementioned general formula (D) and (G) may be added to an organic polar solvent. Then acid dianhydride component represented by the general formula (E) and the compound represented by the general formula (H) may be added in this order to produce a solution of polyamide acid copolymer. Alternatively, the compound represented by the general formula (G) may be added to an organic polar solvent as a diamine component in advance, and then the compound represented by the general formula (E) as an acid dianhydride component, the compound represented by the general formula (C) as a diamine compound, and the compound represented by the general formula (H) may be added in this order to produce a solution of polyamide acid copolymer. Alternatively, the compounds represented by the general formulas (D) and (G) are added to an organic polar solvent in advance as diamine components and then at least two kinds of the compounds represented by the general formulas (E) and (H) are added at the same time to produce a solution of polyamide acid copolymer.

Acid dianhydride and diamine components can be added in reverse order, and substantially the same result can be achieved.

The preferable reaction temperature ranges from −20° C. to 60° C., and the preferable reaction time ranges from 30 minutes to 24 hours.

Example of the organic polar solvents to be used to produce the aforementioned polyamide acid include sulfoxide solvents such as dimethyl sulfoxide and diethyl sulfoxide; formamide solvents such as N,N-dimethylformamide and N,N-diethylformamide; acetamide solvents such as N,N-dimethylacetamide and N,N-diethylacetamide; pyrrolidone solvents such as N-methyl-2-pyrrolidone and N-vinyl-2-pyrrolidone; phenol solvents such as phenol, o-cresol, m-cresol, p-cresol, xylenol, phenol halide, and catechol; hexamethylphosphoramide; and y-butyrolactone. These solvents are can be used alone or in combination thereof, or can be used by mixing aromatic hydrocarbon solvents such as xylene and toluene.

An average molecular weight of the polyamide acid is preferably 5,000 to 1,000,000, more preferably 6,000 to 700,000, and most preferably 10,000 to 300,000. It is not preferable to use the polyamide acid having an average molecular weight of less than 5,000, because polyimide to be produced therefrom has low molecular weight so that such polyimide is too brittle to use as photoreactive resin. Also, it is not preferable to use the polyamide acid having an average molecular weight of more than 1,000,000, because a viscosity of polyamide acid vanish is too high to handle.

Next, thus-obtained polyamide acid can be thermally or chemically imidized to produce a polyimide with a reactive group. In this specification, the term "thermally imidizing method" is a method in which the aforementioned polyamide acid is dehydroimidized by adding tertiary amine thereto. Generally, in the thermally imidized method, polyamide acid can be simply heated to a temperature of 150° C. or more at which polyamide acid is imidized. However, in the present invention, since double bonds and triple bonds in a reactive group usually react at a temperature of 180° C. or more, it is preferred that polyamide acid is thermally imidized at a temperature of 180° C. or less, or chemically imidized at 180° C. or less.

In this specification, the term "chemically imidizing method" is a method in which polyamide acid or a solution thereof is imidized by adding stoichiometric quantity or more of dehydrating agent and catalytic quantity of tertiary amine. An example of dehydrating agents is aliphatic acid dianhydride such as acetic anhydride. Examples of tertiary amines which act as a catalyst include aliphatic tertiary amines and the like such as triethylamine, aromatic tertiary amines and the like such as dimethylaniline, and heterocyclic tertiary amines and the like such as pyridine, picoline, and isoquinoline.

The acid anhydride to be used for synthesizing the aforementioned polyimide is not particularly limited. Any acid anhydrides including the one represented by the general formula (5) can be used. Preferable acid dianhydride has one or three aromatic rings or aliphatic rings.

Examples of acid dianhydrides include: aliphatic or alicyclic tetracarboxylic dianhydride such as butane tetracarboxylic dianhydride, 1,2,3,4-cyclobutane tetracarboxylic dianhydride, 1,3-dimethyl-1,2,3,4-cyclobutane tetracarboxylic acid, 1,2,3,4-cyclopetane tetracarboxylic dianhydride, 2,3,5-tricarboxycyclopentylacetic dianhydride, 3,5,6-tricarboxy norbornane-2-acetic dianhydride, 2,3,4,5tetrahydrofuran tetracarboxylic dianhydride, 5-(2,5dioxysotetrahydrofural)-3-methyl-3-cyclohexene-1,2-dicarboxylic dianhydride, bicyclo[2,2,2]-octo-7-ene-2,3,5,6-tetracarboxylic dianhydride; aromatic tetracarboxylic dianhydride such as pyromellitic dianhydride, 3,3',4,4'-benzophenone tetracarboxylic dianhydride, 3,3',4,4'-biphenylsulfone tetracarboxylic dianhydride, 1,4,5,8-naphtalene tetracarboxylic dianhydride, 2,3,6,7-naphtalene tetracarboxylic dianhydride, 3,3',4,4'-biphenyl ether tetracarboxylic dianhydride, 3,3',4,4'-dimethylphenylsilane tetracarboxylic dianhydride, 3,3',4,4'-tetraphenylsilane tetracarboxylic dianhydride, 1,2,3,4-furantetracarboxylic dianhydride, 4,4'-bis(3,4-dicarboxyphenoxy)diphenyl sulfide dianhydride, 4,4'-bis (3,4-dicarboxyphenoxy) diphenyl sulfonic dianhydride, 4,4'-bis(3,4-dicarboxyphenoxy)diphenylpropane dianhydride, 3,3',4,4,'-perfluoro isopropylidene diphthalic dianhydride, 3,3',4,4'-biphenyltetracarboxylic dianhydride, bis(phthalic acid)phenylphosphine oxide dianhydride, p-phenylene-bis(triphenyl phthalic acid)dianhydride, m-phenylene-bis(triphenyl phthalic acid)dianhydride, 4,4'bis(triphenyl phthalic acid)-diphenyl ether dianhydride, 4,4'-bis(triphenyl phthalic acid)-diphenylmethane dianhydride; and aliphatic tetracarboxylic dianhydride having an aromatic ring such as 1,3,3a,4,5,9b-hexahydro-5(tetrahydro-2,5-dioxo-3-furanyl)-naphtho[1,2-c]furan-1,3-dion, 1,3,3a, 4,5,9b-hexahydro-5-methyl-5-(tetrahydro-2,5-dioxo-3-furany)-naphtho[1,2-c]furan-1,3-dion,1,3,3a,4,5,9b-hexahydro -8-methyl-5-(tetrahydro-2,5-dioxo-3-furanyl-naphtho[1,2-c]furan-1,3-dion, a compound represented by the general formula (6):

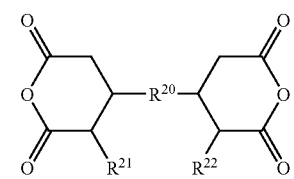

general formula (6)

(wherein $R^{20}$ represents a divalent organic group having an aromatic group, and $R^{21}$ and $R^{22}$ each represent a hydrogen atom or an alkyl group, independently); and a compound represented by the general formula (7):

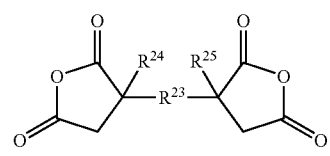

general formula (7)

(wherein $R^{23}$ represents a divalent organic group having an aromatic ring, and $R^{24}$ and $R^{25}$ each represent a hydrogen atom or an alkyl group, independently). These tetracarboxylic dianhydrides can be used alone or in combination of two or more.

In order to synthesize the aforementioned polyimide, not only the diamines represented by the general formulas (1) and (3) but various diamines can also be used. Although these diamines are not particularly limited, examples of diamines include: aromatic diamines such as p-phenylenediamine, m-phenylenediamine, 4,4'-diaminodiphenylmethane, 4,4'diaminodiphenylethane, 4,4'-diaminodiphenyl ether, 4,4'diaminodiphenylsulfide, 4,4'-diaminodiphenylsulfone, 1,5-diaminonaphthalene, 3,3'-dimethyl-4,4'-diaminobiphenyl, 5-amino-1-(4'-aminophenyl)-1,3,3-trimethylindane, 6-amino-1-(4'aminophenyl)-1,3,3-trimethylindane, 4,4'-diaminobenzanilide, 3,5-diamino-3'-trifluoromethylbenzanilide, 3,5-diamino-4'-trifluoromethylbenzanilide, 3,4'-diaminodiphenyl ether, 2,7-diaminofluorene, 2,2-bis(4-aminophenyl)hexafluoropropane, 4,4'-methylene-bis(2-chloroaniline), 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4-diamino-2,2'bis(trifluoromethyl)biphenyl, 2,2-bis[4-(4-aminophenoxy)phenyl]propane, 2,2-bis[4-(4-aminophenoxy)phenyl]hexafluoropropane, 1,4-bis(4-aminophenoxy)benzene, 4,4'-bis(4-aminophenoxy)-biphenyl, 1,3'-bis(4-aminophenoxy)benzene, 9,9-bis(4-aminophenyl)fluorene, 4,4'-(p-phenylene isopropylidene)bisaniline, 4,4'-(m-phenylene isopropylidene)bisaniline, 2,2'-bis[4-(4-amino-2-trifluoromethylphenoxy)phenyl]hexafluoropropane, 4,4'-bis[4-(4-amino-2-trifluoromethyl)phenoxy]-octafluorobiphenyl; aromatic diamines having two amino groups bonded to an aromatic ring such as diamino tetraphenyl thiophene and amino group having a hetero atom in addition to nitrogen atom; aliphatic diamines and alicyclic diamines such as 1,1'-metaxylylenediamine, 1,3-propane diamine, tetramethylene diamine, pentamethylene diamine, octamethylene diamine, nonamethylene diamine, 4,4-diaminoheptanemethylene diamine, 1,4-diaminocyclohexane, isophorone diamine, tetrahydrodicyclopenta dienylene diamine, hexahydro-4,7-methanoindanylene dimethylenediamine, tricyclo[6,2,1,0$^{2.7}$] undecylene dimethyl diamine, and 4,4'-methylenebis(cyclohexylamine); mono-substituted phenylenediamines such as following general formula (8):

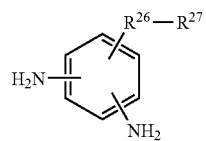

general formula (8)

(wherein $R^{26}$ represents a divalent organic group selected from the group consisting of —O—, —COO—, —OCO—, —CONH—, and —CO— and $R^{27}$ represents a monovalent organic group having a steroid skeleton); and a diamine having a siloxane skeleton represented by the following chemical formula:

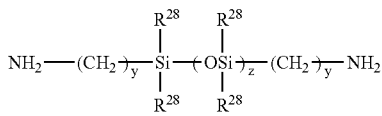

(wherein $R^{28}$ represents a hydrocarbon group having 1 to 12 carbon atoms, y is an integer of 1 to 3, and z is an integer of 1 to 20). These diamine compounds can be used alone or in combination of two or more.

Alternatively, the polyamide of the present invention can be synthesized by: reacting a diamine having a hydroxy group with any acid dianhydride to produce polyamide acid; dehydrating the polyamide acid to effect ring closure to form a polyimide having a hydroxy group; and reacting the polyimide with the acid chloride having a reactive group to introduce the reactive group to a side chain. The synthesizing procedure will be described as follows.

For example, a diamine having a hydroxy group represented by the general formula (9):

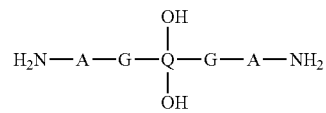

general formula (9)

(wherein A, G, and Q are as defined in the general formula (1)) is reacted with any acid dianhydride to form a polyamide acid. Then the polyamide acid is dehydroimidized, and thereby producing a polyimide having repeating units represented by the general formula (K):

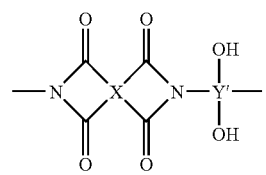

general formula (K)

(wherein X is as defined in the general formula (A) and Y' is a skeleton —A—G—Q—G—A— derived from the diamine represented by the aforementioned general formula (6)).

The aforementioned imidization can be carried out by adding tertiary amine and azeotropic solvent to polyamide acid and then heating them. Examples of tertiary amines include: alkyl ammonium derivatives such as triethylamine and tributylamine; pyridine derivatives such as pyridine, lutidine and picoline; isoquinoline and derivatives thereof; and quinoline. Examples of the azeotropic solvents include aromatic derivatives such as benzene, toluene, and xylene. These solvents are separated from water when they form azeotropic mixtures with water and re-liquefied using a reflux condenser. The separated water is aggressively removed from the reaction system, and thus the imidization proceeds.

Thus-obtained polyimide copolymer solution having repeating units represented by the general formula (K) can be reacted with acid chloride having a reactive group to produce the desired polyimide having repeating units represented by the general formula (A). Alternatively, the polyimide copolymer solution represented by the general formula (K) can be reacted with carboxylic acid having a reactive group and a condensing agent for forming an ester bond to produce the desired polyimide having repeating units represented by the general formula (A).

The polyimide composition according to the present invention can be produced as follows: trimellitic anhydride is reacted with any diamine to form carboxylic acidamide. The carboxylic acidamide is dehydrated to effect ring closure and carboxy-terminated imide oligomer is formed. Then the imide oligomer is reacted with dihydroxy compound derived from cinnamic acid, chalcone, benzalacetophenone, stilbene, coumarin, pyrone, allyl, propargyl, and acetylene to produce an ester bond. Thus the polyimide composition according to the present invention can be produced.

Alternatively, the polyimide composition according to the present invention can be produced by combining the polyimide of the present invention with various organic additives, inorganic fillers, or reinforcements. Such composite materials can be added and blended in any step in the process of synthesizing the polyimide.

The diamine and acid dianhydride of the present invention have reactive groups containing double bonds or triple bonds, so that they exhibit photoreactivity and thermoreactivity derived from this reactive group. The polyimide of the present invention which contains these diamine and acid dianhydride as monomer components also exhibit photoreactivity and thermoreactivity derived from the reaction group. Therefore, the polyimide of the present invention can be suitably used as a photoreactive or thermoreactive resin.

EXAMPLES

The invention will be more clearly understood by referring to the examples which follow. These examples should not be construed to limit the invention in any way.

In the following examples, ESDA indicates 2,2-bis(4-hydroxyphenyl)propane dibenzoate-3,3',4,4'-tetracarboxylic dianhydride, 6FDA indicates 2,2'-hexafluoropropylidene diphthalic dianhydride, DMAc indicates N,N-dimethylacetamide, and DMF indicates N,N-dimethylformamide.

An exothermic peak heating temperature was determined by measuring heat quantities within a range from room temperature to 400° C. by a differential scanning calorimeter DSC CELL SCC-41 (Shimadzu Corp.) at a heating rate of 10° C. per minute under a nitrogen atmosphere.

Weight-average molecular weight was determined by gel permeation chromatography (GPC available from Waters Corporation) under the following conditions:

Column: two columns (KD-806M, Shodex)
Temperature: 60° C.
Detector: RI (Refractive Index)
Flow rate: 1 mL per minute
Developer: DMF(0.03M of lithium bromide and 0.03M of phosphoric acid)
Concentration of sample solution: 0.2 wt %
Injection amount: 20 μl
Reference material: polyethylene oxide Novel diamines according to the present invention were produced in Examples 1 to 8, and novel acid dianhydrides were produced in Examples 9 to 13.

Example 1

(1)Synthesis of 2,2-bis(bromomethyl)-1,3-(m-nitrobenzoate)propane 76.0 g (0.4 mol) of m-nitrobenzoyl chloride and 300 mL of methyl ethyl ketone were placed in a reaction vessel and stirred at 50° C. under a nitrogen atmosphere. Then 47.15 g (0.18 mol) of 2,2-bis(bromomethyl)-1,3-propanediol and 39.5 g (0.5 mol) of pyridine were dissolved in 300 mL of methyl ethyl ketone. The resulting solution was added dropwise in the aforementioned reaction vessel at 50° C., and then refluxed with stirring for 2 hours. Pyridine hydrochloride was precipitated while it was hot, and filtered out. The filtrate was concentrated to about one-fourth of its original volume and cooled to precipitate a solid. The solid was separated from the filtrate by filtration, washed with 200 mL of water, and dried. Thus 95.2 g (94.4% yield) of 2,2-bis(bromomethyl)-1,3-(m-nitrobenzoate)-propane was obtained.

(2)Synthesis of 2,2-bis(4-fluorocinnamic acid methyl ester)-1,3-(m-nitrobenzoate)-propane 38.09 g (68 mmol) of 2,2-bis(bromomethyl)-1,3-(m-nitrobenzoate)-propane of Example 1-(1), 45.6 g (145 mmol) of cesium 4-fluorocinnamate and 250 mL of dimethylformamide were placed in a reaction vessel and heated with stirring at 100° C. to 110° C. under a nitrogen atmosphere for 6 hours. The resulting CsBr was filtered out and the filtrate was poured into water to form a precipitate. The precipitate was separated from the solution by filtration and then dried. Thus 2,2-bis(methyl 4-fluorocinnamate)-1,3-(m-nitrobenzoate)-propane was obtained.

(3)Synthesis of 2,2-bis(methyl 4-fluorocinnamate)-1,3-(m-aminobenzoate)-propane (10)

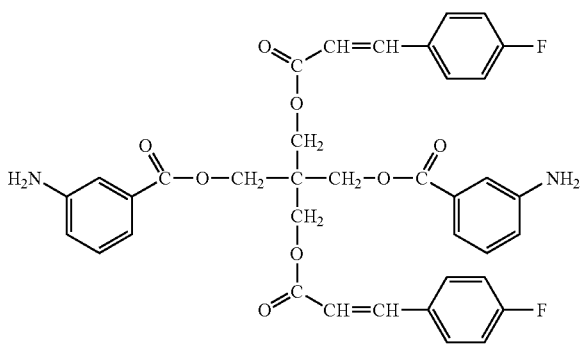

(10)

29.68 g (39 mmol) of 2,2-bis(methyl 4-fluorocinnamoyl)-1,3-(m-nitrobenzoate)-propane, 3 g of 5% Pt-2% Fe-carbon powder (5 wt % of platinum and 2 wt % of iron supported on activated carbon) and 200 mL of dioxane were reacted in a hydrogenation apparatus at 60° C. until hydrogen absorption was completed (hydrogen absorption of 5.6 litter). The reaction mixture was filtered to remove a catalyst and then concentrated. Thus 26 g(99.4% yield) of 2,2-bis (methyl 4-fluorocinnamate)-1,3-(m-aminobenzoate)-propane was obtained.

Example 2

(1)Synthesis of 2-bromoethyl cinnamate 35.3 g (0.212 mol) of cinnamic acid chloride and 100 mL of methyl ethyl ketone were placed in a reaction vessel and stirred at room temperature under a nitrogen atmosphere. Then 28.2 g (0.225 mol) of 2-bromoethanol and 21 g of pylidine were dissolved in 100 mL of methyl ethyl ketone. The resulting solution was added dropwise in the aforementioned reaction vessel at room temperature, and then refluxed with stirring for 2 hours. After cooling the solution, pyridine hydrochloride was precipitated and then separated from the solution by filtration. The filtrate was concentrated and then dissolved in methylene chloride. The solution of methylene chloride was poured into a separating funnel and washed with water. Then the solution was dried with sodium sulfuric anhydride and concentrated. Thus 47 g (86.9% yield) of 2-bromoethyl cinnamate was obtained.

(2) Synthesis of 2,5-dihydroxy terephthalic acid ethyl cinnamate

A mixture of 41.56 g (0.09 mol) of cesium 2-5-dihydroxy terephthalate, 45.9 g (0.18 mol) of 2-bromoethyl cinnamate of Example 2-(1) and 300 mL of DMF was heated with stirring at 100° C. to 110° C. under a nitrogen atmosphere for 6 hours. The resulting CsBr was filtered out and the filtrate was poured into water to form a precipitate. The precipitate was separated from the solution and then dried. Thus 46 g (93.5% yield) of 2,5-dihydroxy terephthalic acid ethyl cinnamate was obtained.

(3) Synthesis of 2,5-bis(m-nitrobenzoate)-terephthalic acid ethyl cinnamate 43.7 g (0.08 mol) of 2,5-dihydroxy terephthalic acid ethyl cinnamate obtained in Example 2-(2), 8 g of pylidine and 400 mL of methyl ethyl ketone were placed in a reaction vessel. Then 26.69 g (0.16 mol) of m-nitrobenzoyl chloride was dissolved in 200 mL of methyl ethyl ketone. The resulting solution was slowly added dropwise in the aforementioned reaction vessel at room temperature, and then refluxed with stirring for 2 hours. The reaction was conducted under a nitrogen atmosphere. After the reaction, the reaction solution was concentrated, washed with water to remove pyridine hydrochloride and then recrystallized. Thus 55 g (81.4% yield) of 2,5-bis(m-nitrobenzoate)-terephthalic acid ethyl cinnamate was obtained.

(4) Synthesis of 2,5-bis(m-aminobenzoate)-terephthalic acid ethyl cinnamate (11)

16.88 g (0.02 mol) of 2,5-bis(m-nitrobenzoate)-terephthalic acid ethyl cinnamate obtained in Example 2-(3), 3 g of 5% Pt-carbon black (5 wt % of platinum supported on carbon black) and 200 mL of dioxane were reacted in a hydrogeneration apparatus at 60° C. until hydrogen absorption was completed (hydrogen absorption of 2.9 litter). The reaction mixture was filtered to remove a catalyst and then concentrated. Thus, 15.68 g (100% yield) of 2,5-bis(m-aminobenzoate)-terephthalic acid ethyl cinnamate (11) was obtained.

Example 3

(1) Synthesis of 2,2-bis(bromomethyl)-1,3-bis(p-nitrobenzoate)-propane 51.08 g (0.19 mol) of 2,2-bis(bromomethyl)-1,3-propanediol, 20 g of pyridine and 200 mL of methyl ethyl ketone were placed in a reaction vessel. Then 74.2 g (0.4 mol) of p-nitrobenzoyl chloride was dissolved in 500 mL of methyl ethyl ketone. The resulting solution was slowly added dropwise in the aforementioned reaction vessel at room temperature, and then refluxed with stirring for 2 hours. The reaction was conducted under a nitrogen atmosphere. After the reaction, the reaction solution was concentrated to about one-second of its original volume. The reaction solution was filtered to remove a solvent and a solid was washed with water to remove pyridine hydrochloride. Thus, 100 g (94% yield) of 2,2-bis(bromomethyl)-1,3-bis(p-nitrobenzoate)-propane was obtained.

(2) Synthesis of 2,2-bis(bromomethyl)-1,3-bis(p-aminobezoate)-propane 56.0 g (0.1 mol) of 2,2-bis(bromomethyl)-1,3-bis(p-nitrobenzoate)-propane, 3 g of 5% Pd carbon powder (5 wt % of Pd supported on activated carbon) and 400 mL of dioxane were reacted in a hydrogeneration apparatus at 60° C. until hydrogen absorption was completed (hydrogen absorption of 14.4 litter). The reaction mixture was filtered to remove a catalyst and then concentrated. Thus 50.0 g (100% yield) of 2,2-bis(bromomethyl)-1,3-bis(p-aminobezoate)-propane was obtained.

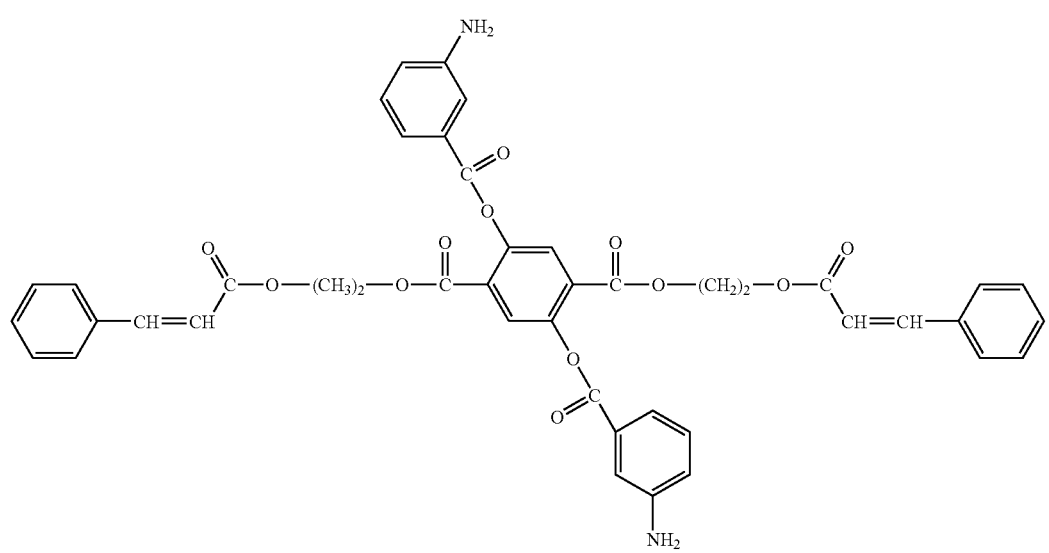

(3)Synthesis of 2,2-bis(coumarin-3-carboxylate methyl)-1,3-bis(p-aminobenzoate)-propane (12)

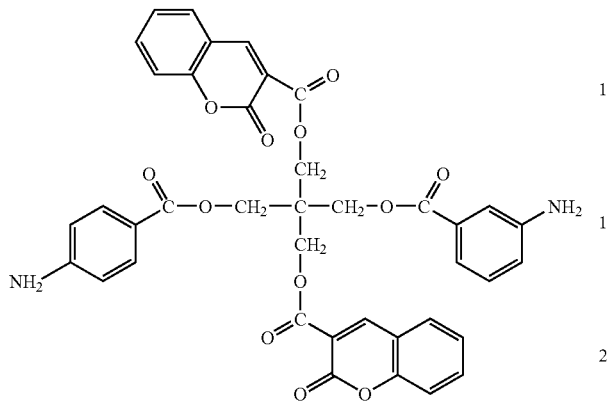

(12)

50 g (0.1 mol) of 2,2-bis(bromomethyl)-1,3-bis(p-aminobezoate)-propane obtained in Example 3(2), 32.2 g (0.1 mol) of cesium coumarin-3-carboxylate and 300 mL of dimethylformamide were place in a reaction vessel and heated with stirring at 100° C. to 110° C. under a nitrogen atmosphere for 6 hours. The resulting CsBr was filtered out and the filtrate was poured into water to form a precipitate. The precipitate was separated from the solution and then dried. Thus 65.3 g (91% yield) of 2,2-bis(coumarin-3-carboxylate methyl)-1,3-bis(p-aminobenzoate)-propane (12) was obtained.

Example 4

(1)Synthesis of 2,5-bis(m-nitrobenzoate)terephthalic acid 19.61 g (0.1 mol) of 2,5-dihydroxy terephthalic acid, 17 g of pyridine and 200 mL of acetone were placed in a reaction vessel. Then 74.22 g (0.4 mol) of m-nitrobenzoyl chloride was dissolved in 400 mL of acetone. The obtained solution was slowly added dropwise in the aforementioned reaction vessel at 50° C. After completion of dropping, the solution was refluxed with stirring for 2 hours. Then the 4 ml of water was added and refluxed with stirring for another 2 hours. After the reaction, the reaction solution was cooled to room temperature to precipitate a solid. The solid was filtered off and then washed with water to remove pyridine hydrochloride. Thus 45 g (90.6% yield) of 2,5-bis(m-nitrobenzoate)terephthalic acid was obtained.

(2)Synthesis of 2,5-bis(m-nitrobenzoate)terephthalic acid chloride 45 g (0.09 mol) of 2,5-bis(m-nitrobenzoate)terephthalic acid obtained in Example 4(1) and 400 mL of ethyl acetate were placed in a reaction vessel. Then 38 g (0.32 mol) of thionyl chloride with a few drops of DMF was added dropwise in the aforementioned reaction vessel at 40° C. and then refluxed with stirring. The reaction was continued until the generation of gas was completed (for about 4 hours). After the reaction, the reaction solution was concentrated. Thus, 45 g (93.8% yield) of 2,5-bis(m-nitrobenzoate)terephthalic acid chloride was obtained.

(3)Synthesis of 2,5-bis(m-nitrobenzoate)terephthalic acid(2-chalcone ester)

35.9 g (0.16 mol) of 2-hydroxychalcone, 20 g of pyridine and 400 mL of methyl ethyl ketone were placed in a reaction vessel. 42.66 g (0.08 mol) of 2,5-bis(m-nitrobenzoate)terephthalic acid chloride obtained in Example 4-(2) was added thereto, and then refluxed with stirring for 2 hours. The reaction solution was concentrated, washed with water, and recrystallized from ethyl acetate. Thus, 62 g (98% yield) of 2,5-bis(m-nitrobenzoate)terephthalic acid(2-chalcone ester) was obtained.

(4)Synthesis of 2,5-bis(m-aminobenzoate)terephthalic acid(2-chalcone ester) (13)

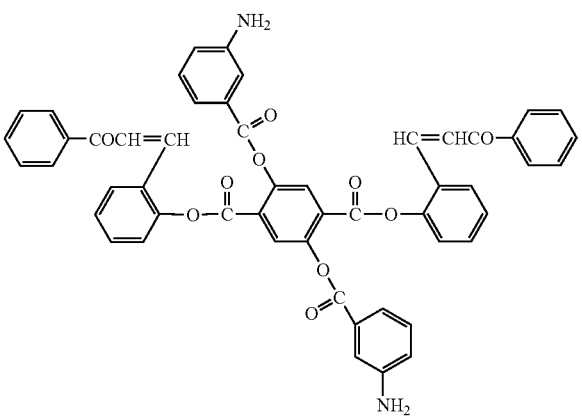

(13)

18.18 g (0.02 mol) of 2,5-bis(m-nitrobenzoate)terephthalic acid(2-chalcone ester) obtained in Example 4-(3), 3 g of 5% Pt-carbon black (5 wt % of platinum supported on carbon black) and 200 mL of dioxane were reacted in a hydrogeneration apparatus at 60° C. until hydrogen absorption was completed (hydrogen absorption of 2.9 litter). The reaction mixture was filtered to remove a catalyst and then concentrated. Thus 17 g (100% yield) of 2,5-bis(m-aminobenzoate)terephthalic acid(2-chalcone ester) (13) was obtained.

Example 5

(1)Synthesis of 2,2-bis(bromomethyl)-1,3-(m-nitrocinnamate)-propane 84.64 g (0.4 mol) of m-nitro cinnamic acid chloride and 300 mL of methyl ethyl ketone were placed in a reaction vessel and stirred at 40° C. under a nitrogen atmosphere. Then, 47.15 g (0.18 mol) of 2,2-bis(bromomethyl)-1,3-propanediol and 39.5 g (0.5 mol) of pyridine were dissolved in 300 mL of methyl ethyl ketone, and the obtained solution was added dropwise in the aforementioned reaction vessel at 40° C. After completion of dropping, the solution was refluxed with stirring for 2 hours. Pyridine hydrochloride was precipitated while it was hot, and then separated from the solution by filtration. The filtrate was concentrated to about one-fourth of its original volume and cooled to precipitate a solid. The solid was filtered out, washed with 200 mL of water, and dried. Thus 91.7 g (83.2% yield) of 2,2-bis(bromomethyl)-1,3-(m-nitrocinnamate)-propane was obtained.

(2)Synthesis of 2,2-bis(cinnamic acid methyl ester)-1,3-(m-nitrocinnamate)-propane 61.1 g(0.1 mol) of 2,2-bis(bromomethyl)-1,3-(mnitrocinnamate)-propane obtained in Example 5-(1), 56.0 g (0.2 mol) of cesium cinnamate and 350 mL of dimethylformamide were placed in a reaction vessel, and heated with stirring at 100° C. to 110° C. under a nitrogen atmosphere for 6 hours. The resulting CsBr was filtered out and the filtrate was poured into water to form a precipitate. The precipitate was separated from the solution and then dried. Thus 70 g (93.7% yield) of 2,2-bis(cinnamic acid methyl ester)-1,3-(m-nitrocinnamate)-propane was obtained.

(3)Synthesis of 2,2-bis(cinnamic acid methyl ester)-1,3-(m-aminocinnamate)-propane (14)

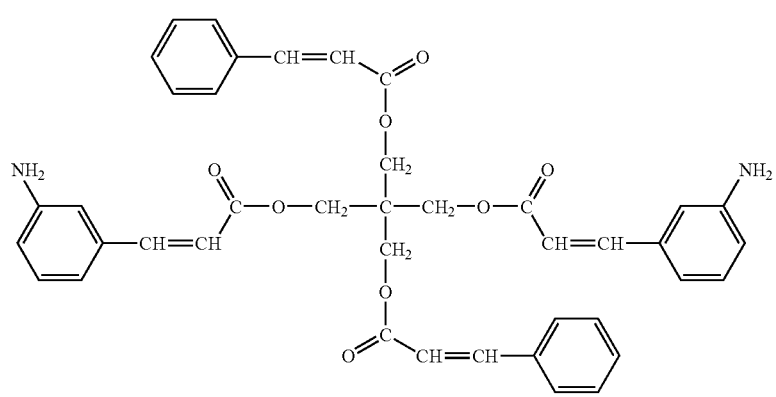

(14)

22.36 g (30 mol) of 2,2-bis(cinnamic acid methyl ester)-1,3-(m-nitrocinnamate)-propane obtained in Example 5-(2), 3 g of 5% Pt-2% Fe-carbon powder (5 wt % of platinum and 2 wt % of iron supported on activated carbon) and 200 mL of dioxane were reacted in a hydrogenation apparatus at 60° C. until hydrogen absorption was completed (hydrogen absorption of 4.3 litter). The reaction mixture was filtered to remove a catalyst and then concentrated. Thus 20.56 g (99.8% yield) of 2,2-bis(cinnamic acid methyl ester)-1,3-(m-aminocinnamate)-propane (14) was obtained.

Example 6

(1)Synthesis of 1,4-bis cinnamic acid benzene-2-carboxylic acid 15.4 g (0.1 mol) of 2,5-dihydroxybenzoic acid, 31.6 g (0.4 mol) of pyridine and 150 mL of acetone was placed in a reaction vessel and stirred at room temperature. 58.3 g (0.35 mol) of cinnamic acid chloride were dissolved in 150 mL of acetone, added dropwise to the mixture, and then refluxed with stirring for 2 hours. 30 mL of water was added to the reaction solution and refluxed with stirring for another 2 hours. The solution was concentrated and washed with water and toluene. Thus 35 g of 1,4-bis cinnamic acid benzene-2-carboxylic acid was obtained.

(2)Synthesis of 1,4-bis cinnamic acid benzene-2-carboxylic chloride 12.43 g (30 mmol) of 1,4-bis cinnamic acid benzene-2-carboxylic acid was dissolved in 100 mL of ethyl acetate. 30 g of thionyl chloride with a few drops of DMF was slowly added dropwise thereto and then refluxed for 4 hours. The reaction solution was concentrated. Thus 12.8 g of 1,4-bis cinnamic acid benzene-2-carboxylic chloride was obtained.

(3)Synthesis of 1,4-bis cinnamic acid benzene-2-carboxylic acid-3,5-dinitrobenzil alcohol ester 5.94 g (30 mmol) of 3,5-dinitrobenzil alcohol, 100 mL of methyl ethyl ketone (hereinafter referred to as MEK) and 7.9 g of (0.1 mol) of pyridine were placed in a reaction vessel. 12.8 g (30 mmol) of 1,4-bis cinnamic acid benzene-2-carboxylic acid chloride was dissolved in 150 mL of acetone, slowly added dropwise in the reaction vessel, and then refluxed with stirring for 2 hours. The reaction solution was concentrated and washed with water. The solution was then filtered, dried and recrystallized. Thus, 16 g of 1,4-bis cinnamic acid benzene-2-carboxylic acid-3,5-dinitrobenzil alcohol ester was obtained.

(4)Synthesis of 1,4-bis cinnamic acid benzene-2-carboxylic acid-3,5-diaminobenzil alcohol ester 14.4 g (25 mmol) of 1,4-bis cinnamic acid benzene-2-carboxylic acid-3,5-dinitrobenzil alcohol ester, 3 g of 5% Pt-2% Fe-carbon powder (5 wt % of platinum and 2 wt % of iron supported on activated carbon) and 200 mL of dioxane was reacted in a hydrogenation apparatus at 60° C. until hydrogen absorption was completed (hydrogen absorption of 3.6 litter). The reaction mixture was filtered to remove a catalyst and then concentrated. Thus 12.9 g of 1,4-bis cinnamic acid benzene-2-carboxylic acid-3,5-diaminobenzil alcohol ester was obtained.

Example 7

(1)Synthesis of 2-bromoethyl cinnamate 35.3 g (0.212 mol) of cinnamic acid chloride and 100 mL of methyl ethyl ketone were placed in a reaction vessel and stirred under a nitrogen atmosphere. 28.2 g (0.225 mol) of 2-bromoethanol and 21 g of pyridine were dissolved in 100 mL of methyl ethyl ketone and added dropwise in the aforementioned reaction vessel. After completion of dropping, the solution was refluxed with stirring for 2 hours and cooled. Pyridine hydrochloride was precipitated, and then separated from the solution by filtration. The filtrate was concentrated and then dissolved in methylene chloride. The solution of methylene chloride was poured into a separating funnel and washed with water. Then the solution was dried with anhydrous sodium sulfate and concentrated. Thus 47 g of 2-bromoethyl cinnamate was obtained.

(2)Synthesis of 2-hydroxyterephthalic acid ethylcinnamate 33.44 g (0.75 mol) of 2-dicesium salt of 2-hydroxy terephthalic acid, 38.27 g (0.15 mol) of 2-bromoethyl cinnamate and 200 mL of DMF were placed in a reaction vessel and reacted at 110° C. for 5 hours under a nitrogen atmosphere. After reaction, the precipitated CsBr was filtered out and the filtrate was poured into 800 mL of water to form a precipitate. The precipitate was separated from the solution and then dried. Thus 32 g (0.06 mol) of 2-hydroxy terephthalic acid ethyl cinnamate was obtained.

(3)Synthesis of 3,5-dinitrobenzoic acid ester-2-terephthalic acid ethyl cinnamate 32 g (0.06 mol) of 2-hydroxy terephthalic acid ethyl cinnamate, 7.9 g (0.1 mol) of pyridine and 200 mL of MEK were placed in a reaction vessel and stirred at room temperature. 16.09 g (0.06 mol) of 3,5-dinitrobenzoylchloride was dissolved in 100 mL of MEK and added dropwise in the reaction vessel. After completion of dropping, the solution was refluxed with stirring for 2 hours. The reaction solution was then concentrated, washed with water, and dried. Thus 40 g (0.052 mol) of 3,5-dinitrobenzoic acid ester-2-terephthalic acid ethyl cinnamate was obtained.

(4)Synthesis of 3,5-diaminobenzoic acid ester-2-terephthalic acid ethyl cinnamate 38.12 g (0.05 mol) of 3,5-dinitrobenzoic acid ester-2-terephthalic acid ethyl cinnamate was reduced under the same conditions as Example 1. Thus 35.12 g (0.05 mol) of 3,5-diaminobenzoic acid ester-2-terephthalic acid ethyl cinnamate was obtained.

Example 8

(1)Synthesis of 1,3-dichloropropane-2-(3,5-dinitrobenzoate)

26.82 g (0.1 mol) of 3,5-dinitrobenzoyl chloride was dissolved in 200 mL of acetone. 14.19 g (0.11 mol) of 1,3-dichloro-2-propanol was dissolved in 150 mL of pyridine and added dropwise to the above solution. After completion of dropping, the mixture solution was refluxed with stirring for 2 hours. The reaction solution was poured into 1 liter of water to form a precipitate. The precipitate was separated from the solution and then dried to produce 36.4 g of a solid. Upon recrystallization from acetone/hexane mixed solvent, 32 g of 1,3-dichloropropane-2-(3,5-dinitrobenzoate) was obtained.

(2)Synthesis of 1,3-bis(cinnamic acid)propane-2-(3,5-dinitrobenzoate)

18.04 g (50 mmol) of 1,3-dichloropropane-2-(3,5-dinitrobenzoate), 33.6 g (120 mmol) of cesium cinnamate and 150 mL of DMF were placed in a reaction vessel and reacted at 100° C. under a nitrogen atmosphere for 12 hours. After reaction, the precipitated CsCl was filtered out. The filtrate was concentrated and was subjected to column purification (acetone/silica gel). Thus 23.4 g of 1,3-bis(cinnamic acid) propane-2-(3,5-dinitrobenzoate) was obtained.

(3)Synthesis of 1,3-bis(cinnamic acid)propane-2-(3,5-aminobenzoate)

14.6 g (25 mmol) of 1,3-bis(cinnamic acid)propane-2-(3, 5-dinitrobenzoate) was reduced in the same manner as described in Example 6. Thus 13.1 g (25 mmol) of 1,3-bis (cinnamic acid)propane-2-(3,5-aminobenzoate) was obtained.

Example 9

(1)Synthesis of 2,5-dihydroxy allyl benzoate 154.12 g (1 mol) of 2,5-dihydroxy benzoic acid and 162.91 g (0.4 mol) of cesium carbonate were dissolved in a mixed solution of 300 mL of acetone and 300 mL of water, and then concentrated and dried. Thus 286.0 g of 2,5-dihydroxy cesium benzoate was obtained.

71.5 g (0.25 mol) of 2,5-dihydroxy cesium benzoate, 30.25 g (0.25 mol) of allyl bromide and 140 mL of DMF were placed in a reaction vessel and reacted at 100° C. for 2 hours under a nitrogen atmosphere. The resulting CsBr was filtered out and the filtrate was poured into 500 mL of water. The extracted oil layer was concentrated and dried. Thus 43.7 g (90% yield) of 2,5-dihydroxy allyl benzoate was obtained.

(2)Synthesis of 2,5-allyl benzoate-dibenzoate-3,3',4, 4'-tetracarboxylic dianhydride 44.22 g (0.21 mol) of trimellitic chloride and 150 mL of methyl ethyl ketone were placed in a reaction vessel. 19.42 g (0.1 mol) of 2,5-dihydroxy allyl benzoate was dissolved in 25 g of pyridine and 100 mL of methyl ethyl ketone, and added dropwise in the reaction vessel. After completion of dropping, the solution was refluxed with stirring for 2 hours. The reaction solution was concentrated, washed with water and dried. Upon recrystallization from acetic anhydride, 43 g (79.3 mmol, 79.3% yield) of 2,5-allyl benzoate-dibenzoate-3,3',4,4'-tetracarboxylic dianhydride was obtained.

Example 10

Synthesis of 2,5-propargylbenzoic acid-dibenzoate-3,3',4,4'-tetracarboxylic dianhydride In the same manner as described in Example 9, the aforementioned acid dianhydride was obtained using propargyl bromide as a substitute for allyl bromide.

Example 11

(1) Synthesis of 2-bromoethyl cinnamate 83.3 g (0.5 mol) of cinnamic acid chloride and 200 mL of methyl ethyl ketone were placed in a reaction vessel. 62.5 g (0.5 mol) of 2-bromoethanol and 50 g of pyridine were added dropwise in the reaction vessel. The solution was refluxed with stirring for 2 hours under a nitrogen atmosphere and then concentrated. 100 mL of water was added to the concentrated solution. After extraction with chloroform, dehydration with anhydrous sodium sulfate, concentration, and drying, 121 g of 2-bromoethyl cinnamate was obtained.

(2) Synthesis of 2,5-dihydroxy terephthalic acid bis(2-ethyl cinnamate)

46.2 g (0.1 mol) of cesium 2,5-dihydroxy terephthalate, 51.02 g (0.2 mol) of 2-bromoethyl cinnamate and 200 mL of DMF were placed in a reaction vessel and reacted at 100° C. for 2 hours under a nitrogen atmosphere. The resulting CsBr was filtered out and the filtrate was poured into 1000 mL of ice water to precipitate a solid. The solid was separated from the solution and then dried. Thus 46.5 g (85% yield) of 2,5-dihydroxy terephthalic acid bis(2-ethyl cinnamate) was obtained.

(3) Synthesis of 2,5-{terephthalic acid bis(2-ethyl cinnamate)}-dibenzoate-3,3',4,4'-tetracarboxylic dianhydride 31.59 g (0.15 mol) of trimellitic chloride and 150 mL of methyl ethyl ketone were placed in a reaction vessel. 38.26 g (0.07 mol) of 2,5-dihydroxy terephthalic acid bis(2-ethyl cinnamate) was dissolved in 15 g of pyridine and 100 ml of methyl ethyl ketone, and added dropwise to the reaction vessel. After completion of dropping, the solution was refluxed with stirring for 2 hours. The reaction solution was concentrated, washed with water, and dried. Upon recrystallization from acetic anhydride, 43.8 g (48.9 mmol, 70% yield) of 2,5-{terephthalic acid bis(2-ethyl cinnamate)}-dibenzoate-3,3',4,4'-tetracarboxylic dianhydride was obtained.

Example 12

(1) Synthesis of 2,2-bis(coumarin-3-carboxy-methyl)-1,3-propanediol 26.19 g (0.1 mol) of 2,2-bis(bromomethyl)-1,3-propanediol, 64.41 g (0.2 mol) of cesium coumarin-3-carboxylate and 150 mL of DMF were placed in a reaction vessel and reacted at 100° C. for 2 hours under a nitrogen atmosphere. The resulting CsBr was filtered out and the filtrate was poured into 1000 mL of ice water to precipitate a solid. The solid was separated from the solution and then dried. Thus 42.28 g (88% yield) of 2,2-bis(coumarin-3-carboxylic acid methyl)-1,3-propanediol was obtained.

(2) Synthesis of 2,2-bis(coumarin-3-carboxylic acid methyl)-1,3-propane dibenzoate-3,3',4,4'-tetracarboxylic dianhydride 31.59 g (0.15 mol) of trimellitic chloride and 150 ml of methyl ethyl ketone were placed in a reaction vessel. 33.6 g (0.07 mol) of 2,2-bis(coumarin-3-carboxylic acid methyl)-1,3-propanediol was dissolved in 15 g of pyridine and 100 mL of methyl ethyl ketone, and added dropwise in the reaction vessel. After completion of dropping, the solution was refluxed with stirring for 2 hours. The reaction solution was concentrated and washed with water. Then the solution was heated with acetic anhydride for an hour, and then concentrated. Thus 33.15 g (40 mmol, 57% yield) of 2,2-bis(coumarin-3-carboxylic acid methyl)-1,3-propane dibenzoate-3,3',4,4'-tetracarboxylic dianhydride was obtained.

Example 13

(1) Synthesis of 3-bromo propionate-7-coumarin 48.64 g (0.3 mol) of 7-hydroxy coumarin, 32 g of pyridine, and 300 mL of methyl ethyl ketone were placed in a reaction vessel. 51.42 g (0.3 mol) of 3-bromopropionyl chloride and 200 mL of methyl ethyl ketone were added dropwise in the reaction vessel. The solution was refluxed with stirring for 2 hours and then concentrated. 100 mL of water was added to the concentrated solution. After extraction with chloroform, dehydration with anhydrous sodium sulfate, concentration, and drying, 78.3 g of 3-bromo propionate-7-coumarin was obtained.

(2) Synthesis of 2,5-dihydroxy naphthalene carboxylic acid-3-propionate-7-coumarin 29.71 g (0.1 mol) of 3-bromo propionate-7-coumarin, 33.60 g (0.1 mol) of cesium 2,5-dihydroxy naphthalene carboxylate and 150 mL of DMF were placed in a reaction vessel and reacted at 100° C. under a nitrogen atmosphere for 2 hours. The resulting CsBr was filtered out, and the filtrate was poured into 1000 mL of ice water to precipitate a solid. The solid was separated from the solution and then dried. Thus 33.6 g (0.08 mol) of 2,5-dihydroxy naphthalene carboxylic acid-3-propionate-7-coumarin was obtained.

(3) Synthesis of 2,5-(dihydroxynaphthalene carboxylic acid-3-propionate-7-coumarin)-dibenzoate-3,3',4,4'-tetracarboxylic dianhydride 31.59 g (0.15 mol) of trimellitic chloride and 150 mL of methyl ethyl ketone were placed in a reaction vessel. 29.4 g (0.07 mol) of 2,5-dihydroxy naphthalene carboxylic acid-3-propionate-7-coumarin was dissolved in 15 g of pyridine and 100 mL of methyl ethyl ketone, and added dropwise in the reaction vessel. After completion of dropping, the solution was refluxed with stirring for 2 hours. The reaction solution was concentrated, washed with water, and dried. Upon recrystallization from acetic anhydride, 38.4 g (50 mmol, 71% yield) of 2,5-(dihydroxynaphthalene carboxylic acid-3-propionate-7-coumarin)-dibenzoate-3,3',4,4'-tetracarboxylic dianhydride was obtained.

In the following Examples 14 to 28, a novel polyimide composition was produced from the novel diamine and acid dianhydride obtained in the aforementioned Examples 1 to 13.

Example 14

20.12 g (30 mmol) of 2,2-bis(4-fluorocinnamic acid methyl ester)-1,3-(m-aminobenzoate)-propane (10) obtained in Example 1, 17.3 g of ESDA (30 mmol) and 70 g of DMF were placed in a reaction vessel and stirred in an ice bath for 30 minutes to produce a polyamide acid solution. 15 g of acetic anhydride, 10 g of β-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg (6.6×10$^{-3}$ atm), for one night). Thus 36 g of polyimide (having a weight average molecular weight of 92,000) was obtained.

Example 15

15.68 g (0.02 mol) of 2,5-bis(m-aminobenzoate)terephthalic acid ethyl cinnamate (11) obtained in Example 2, 8.88 g (0.02 mol) of 6FDA and 100 g of DMF were placed in a reaction vessel, and stirred in an ice bath for 30 minutes to produce a polyamide acid solution. 10 g of acetic anhydride, 5 g of β-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg (6.6×10$^{-3}$ atm), for one night). Thus 23 g (96.5% yield) of polyimide (having a weight average molecular weight of 110,000) was obtained.

Example 16

14.36 g (0.02 mol) of 2,2-bis(coumarin-3-carboxylate methyl)-1,3-bis(p-aminobenzoate)-propane (12) obtained in Example 3, 8.61 g (0.02 mol) of BAPS-M and 180 mL of DMF were placed in a reaction vessel. In addition, 11.53 g (0.02 mol) of ESDA and 8.88 g (0.02 mol) of 6FDA were added in the reaction vessel and stirred in an ice bath for 30 minutes to produce a polyamide acid solution. 10 g of acetic anhydride, 5 g of β-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg (6.6×10$^{-3}$ atm), for one night). Thus 41 g (78% yield) of polyimide (having a weight average molecular weight of 95,000) was obtained.

Example 17

17 g (0.02 mol) of 2,5-bis(m-aminobenzoate)terephthalic acid(2-chalcone ester) (13) obtained in Example 4 and 100 mL of DMF were placed in a reaction vessel. In addition, 8.88 g (0.02 mol) of 6FDA was added in the reaction vessel and stirred in an ice bath for 30 minutes to produce a polyamide acid solution. 10 g of acetic anhydride, 5 g of P-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg (6.6×10$^{-3}$ atm), for one night). Thus 24.5 g (97.4% yield) of polyimide (having a weight average molecular weight of 87,000) was obtained.

Example 18

20.56 g (30 mol) of 2,2-bis(cinnamic acid methyl ester)-1,3-(m-aminocinnamate)-propane (14) obtained in Example 5, 17.3 g (30 mmol) of ESDA and 70 g of DMF were placed in a reaction vessel and stirred at room temperature for 30 minutes to produce a polyamide acid solution. 15 g of acetic anhydride, 10 g of β-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg (6.6×10$^{-3}$ atm), for one night). Thus 35 g (95.2% yield) of polyimide (having a weight average molecular weight of 80,000) was obtained.

Example 19

12.9 g (25 mmol) of 1,4-bis cinnamic acid benzene-2-carboxylic acid-3,5-diaminobenzil alcohol ester obtained in Example 6, 14.4 g (25 mmol) of ESDA and 70 g of DMF were placed in a reaction vessel and stirred for 30 minutes to produce a polyamide acid solution. 15 g of acetic anhydride, 10 g of β-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg, for one night). Thus 26 g of polylmide composition (having a weight average molecular weight of 58,000) was obtained.

Example 20

17.56 g (25 mmol) of 3,5-diaminobenzoic acid ester-2-terephthalic acid ethyl cinnamate obtained in Example 7, 14.4 g (25 mmol) of ESDA and 70 g of DMF were placed in a reaction vessel and stirred for 30 minutes to produce a polyamide acid solution. 15 g of acetic anhydride, 10 g of β-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg, for one night). Thus 35 g of polyimide composition (having a weight average molecular weight of 50,000) was obtained.

Example 21

14.6 g (25 mmol) of 1,3-bis(cinnamic acid)propane-2-(3, 5-dinitrobenzoate) obtained in Example 8, 22.21 g (50 mmol) of 6FDA, 10.76 g (25 mmol) of bis[4-(3-aminophenoxy)phenyl]sulfone and 110 g of DMF were placed in a reaction vessel and stirred for 30 minutes to produce a polyamide acid solution. 15 g of acetic anhydride, 10 g of β-picoline and 50 g of DMF were added to the polyamide acid solution and stirred at room temperature for an hour and subsequently at 120° C. for an hour. The solution was poured into methanol to precipitate a solid. Separated from the solution by filtration, the solid was crushed and dried in a vacuum oven (90° C., 5 mmHg, for one night). 45 g of polyimide composition (having a weight average molecular weight of 48,000) was obtained.

Example 22

4.33 g (0.01 mol) of bis[4-(3-aminophenoxy)phenyl]sulfone and 30 g of DMAc were placed in a 300 mL separable flask equipped with a stirrer. Then 5.42 g (0.01 mol) of acid dianhydride obtained in Example 9 was added at a dash with vigorous stirring, and continuously stirred for 30 minutes.

The imidization reaction was carried out by adding 0.93 g (0.02 mol) of β-picoline, 5 g of acetic anhydride and 10 g of DMAc to the above reaction solution and heating the solution to about 120° C. The reaction was carried out under a nitrogen atmosphere. After the reaction, the solution was poured into methanol for precipitation, and then filtered and dried. Thus 9.0 g of white powder of polyimide composition was obtained. A weight average molecular weight of the white powder of polyimide composition was 70,000.

Example 23

4.33 g (0.01 mol) of bis[4-(3-aminophenoxy)phenyl]sulfone and 30 g of DMAc were placed in a 300 mL separable flask equipped with a stirrer. Then 5.42 g (0.01 mol) of acid dianhydride obtained in Example 10 was added at a dash with vigorous stirring, and continuously stirred for 30 minutes.

The imidization reaction was carried out by adding 0.93 g (0.02 mol) of β-picoline, 5 g of acetic anhydride and 10 g of DMAc to the above reaction solution and heating the solution to about 120° C. The reaction was carried out under a nitrogen atmosphere.

After the reaction, the solution was poured into methanol for precipitation, and then filtered and dried. Thus 9.1 g of white powder of polyimide composition was obtained. A weight average molecular weight of the powder of polyimide composition was 60,000.

Example 24

4.33 g (0.01 mol) of bis[4-(3-aminophenoxy)phenyl]sulfone and 30 g of DMAc were placed in a 300 mL separable flask equipped with a stirrer. Then 8.96 g (0.01 mol) of acid dianhydride obtained in Example 11 was added at a dash with vigorous stirring, and continuously stirred for 30 minutes.

The imidization reaction was carried out by adding 0.93 g (0.02 mol) of β-picoline, 5 g of acetic anhydride and 10 g of DMAc to the above reaction solution and heating the solution to about 120° C. The reaction was carried out under a nitrogen atmosphere.

After the reaction, the solution was poured into methanol for precipitation, and then filtered and dried. Thus 12.2 g of yellow powder of polyimide composition was obtained. A weight average molecular weight of the yellow powder of polyimide composition was 55,000.

Example 25

4.33 g (0.01 mol) of bis[4-(3-aminophenoxy)phenyl]sulfone and 30 g of DMAc were placed in a 300 mL separable flask equipped with a stirrer. Then 8.29 g (0.01 mol) of acid dianhydride obtained in Example 12 were added at a dash with vigorous stirring, and continuously stirred for 30 minutes.

The imidization reaction was carried out by adding 0.93 g (0.02 mol) of β-picoline, 5 g of acetic anhydride and 10 g of DMAc to the above reaction solution and heating the solution to about 120° C. The reaction was carried out under a nitrogen atmosphere.

After the reaction, the solution was poured into methanol for precipitation, and then filtered and dried. Thus 12.0 g of white powder of polyimide composition was obtained. A weight average molecular weight of the white powder of polyimide composition was 58,000.

Example 26

4.33 g (0.01 mol) of bis[4-(3-aminophenoxy)phenyl]sulfone and 30 g of DMAc were placed in a 300 mL separable flask equipped with a stirrer. Then 7.68 g (0.01 mol) of acid dianhydride obtained in Example 13 was added at a dash with vigorous stirring, and continuously stirred for 30 minutes.

The imidization reaction was carried out by adding 0.93 g (0.02 mol) of β-picoline, 5 g of acetic anhydride and 10 g of DMAc to the above reaction solution and heating the solution to about 120° C. The reaction was carried out under a nitrogen atmosphere.

After the reaction, the solution was poured into methanol for precipitation, and then filtered and dried. Thus 11.2 g of white powder of polyimide composition was obtained. A weight average molecular weight of the white powder of polyimide composition was 65,000.

Example 27

12.9 g (25 mmol) of 1,4-bis cinnamic acid benzene-2-carboxylic acid-3,5-diaminobenzil alcohol ester obtained in Example 6 and 70 g of DMF were placed in a reaction vessel. Then 23.27 g (25 mmol) of the powdered 2,5-{terephthalic acid bis(2-ethyl cinnamate)}-dibenzoate-3,3',4,4'-tetracarboxylic dianhydride obtained in Example 11 was added in the reaction vessel and stirred for 30 minutes (this reaction was carried out under a nitrogen atmosphere in an ice bath).

10 g of acetic anhydride, 2.5 g of β-picoline and 50 g of DMF were added to the above reaction solution and stirred at room temperature for 2 hours and at 100° C. for an hour. This solution was poured into 2 litres of methanol for precipitation. The precipitated resin was filtered out, purified using the Soxhlet extractor (solvent methanol), and then dried. Thus 33 g of polyimide composition was obtained.

Example 28

16.76 g (25 mmol) of 2,2-bis(4-fluorocinnamic acid methyl ester)-1,3-(m-aminobenzoate)-propane obtained in Example 1 and 80 g of DMF were placed in a reaction vessel. Then 23.27 g (25 mmol) of 2,5-{terephthalic acid bis(2-ethyl cinnamate)}-dibenzoate-3,3',4,4'-tetracarboxylic dianhydride obtained as powder in Example 11 was added in the reaction vessel and stirred for 30 minutes (this reaction was carried out under a nitrogen atmosphere in an ice bath).

10 g of acetic anhydride, 2.5 g of β-picoline and 50 g of DMF were added to the above reaction solution and stirred at room temperature for 2 hours and at 100° C. for an hour. This solution was poured into 2 litres of methanol for precipitation. The precipitated resin was filtered out, purified using the Soxhlet extractor (solvent methanol), and then dried. Thus 37 g of polyimide composition was obtained.

(Evaluation of Photosensitivity)

The novel polyimide compositions obtained in Examples 14 to 28 according to the present invention each were dissolved in 1,3-dioxolane. Then each polyimide composition solution was applied to a 125-μm-thick polyimide film APICAL NP available from Kaneka Corporation and dried to produce a 5 μm-thick film of photosensitive composition.

A pattern mask with a line/space ratio=100/100 μm was put on the film and then the film was exposed to parallel light having a total light energy of 5J/cm$^2$ (wavelength of 400 nm). The film was then developed using a solution of butyl cellosolve/dioxolane=50/50. In this way, a pattern of 100/100 μm was formed.

INDUSTRIAL APPLICABILITY

The present invention makes it possible to produce a diamine having 2 to 4 reactive groups containing a double bond or triple bond, an acid dianhydride having a reactive group derived from the group consisting of cinnamic acid, chalcone, benzalacetophenone, stilbene, coumarin, pyrone, allyl, propargyl, and acetylene, and a polyimide containing the diamine and the acid dianhydride as monomer components. The diamine and the acid dianhydride of the present invention exhibit photoreactivity and thermoreactivity derived from this reactive group. The polyimide of the present invention which contains the diamine and acid dianydride as monomer components also exhibit photoreactivity and thermoreactivity derived from the reaction group. Therefore, the polyimide of the present invention can be suitably used as a photoreactive or thermoreactive resin.

What is claimed is:

1. A diamine comprising 2 to 4 organic groups containing at least one carbon—carbon double bond or triple carbon—carbon bond, wherein a first organic group in which at least the two organic groups having at least one double bond or triple bond are bonded is bonded to a second and a third organic groups to each of which an amino group is bonded, by the medium of a divalent organic group selected from the group consisting of —O—, —CO—, —COO—, —OCO—, —NH—, —NHCO—, and —CONH—.

2. The diamine according to claim 1, wherein said diamine has a structure represented by the general formula (1)

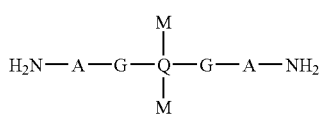

general formula (1)

wherein A and G each represent a divalent organic group, G is a divalent organic group selected from the group consisting of —O—, —CO—, —COO—, —OCO—, —NH—, —NHCO—, and —CONH—, Q represents a tetravalent organic group, and M represents RCOO— or ROCO—, wherein R represents a monovalent organic group having a reactive group selected from the following group (II)

Group (II)

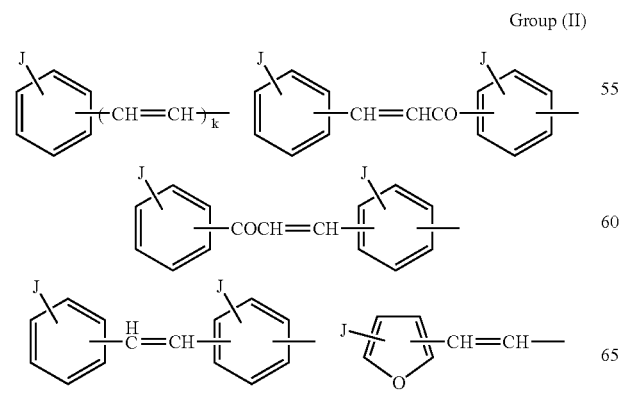

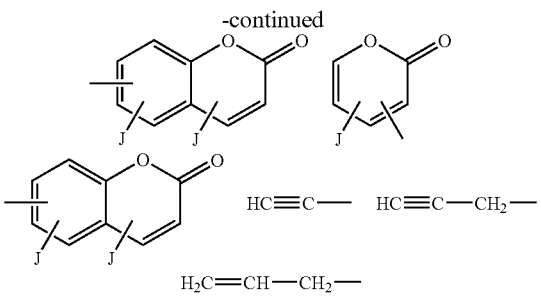

(wherein k is an integer of 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof).

3. The diamine according to claim 1, wherein in the general formula (1) is a divalent organic group selected from the group consisting of Group (I)

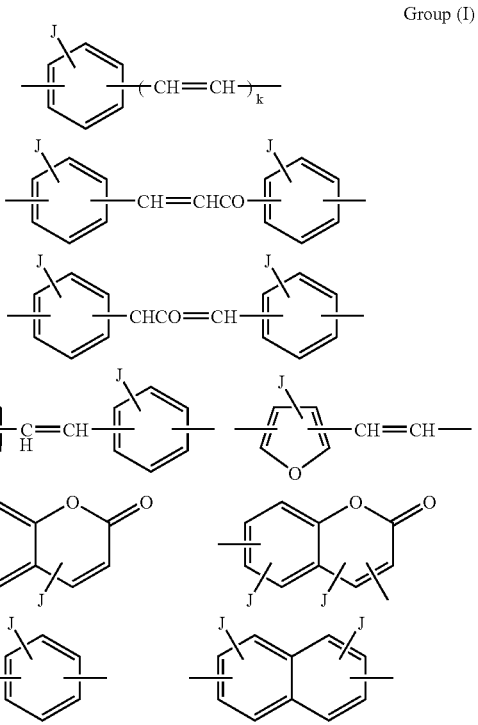

wherein k is an integer of 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof.

4. The diamine according to claim 2, wherein Q in the general formula (1) is a tetravalent aliphatic hydrocarbon group having 2 to 20 carbon atoms and a tetravalent organic group selected from the group consisting of

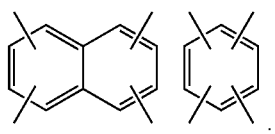

5. The diamine according to claim 2, wherein R in the general formula (1) is a monovalent organic group selected from the group (III) consisting of Group (III)

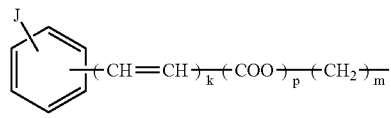

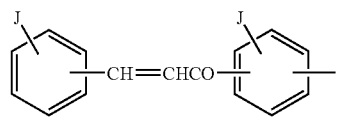

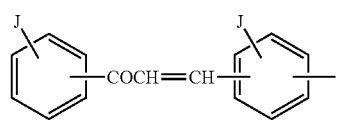

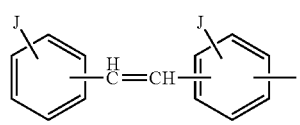

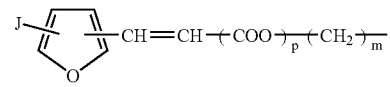

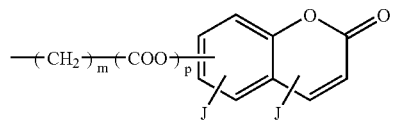

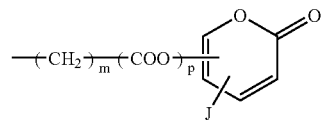

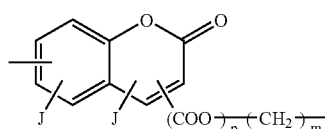

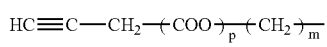

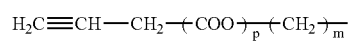

wherein k is 1 or 2, J is a group capable of arbitrarily substituting for hydrogen atom of an aromatic ring and independently represents halogen, C1 to C3 alkyl, C1 to C3 alkoxy, or C1 to C3 fluoroalkyl, or a combination thereof, m is an integer of 0 to 20, p is 0 when m is 0 or 1 or p is 1 when m is 2 or more.

6. The diamine according to claim 1, which is selected from the group consisting of the following compounds:

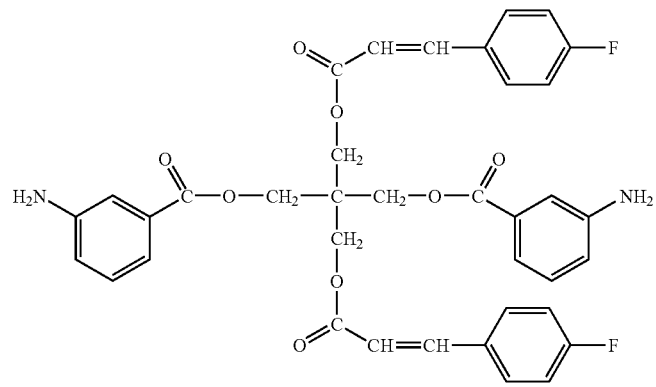

(IO)

(11)
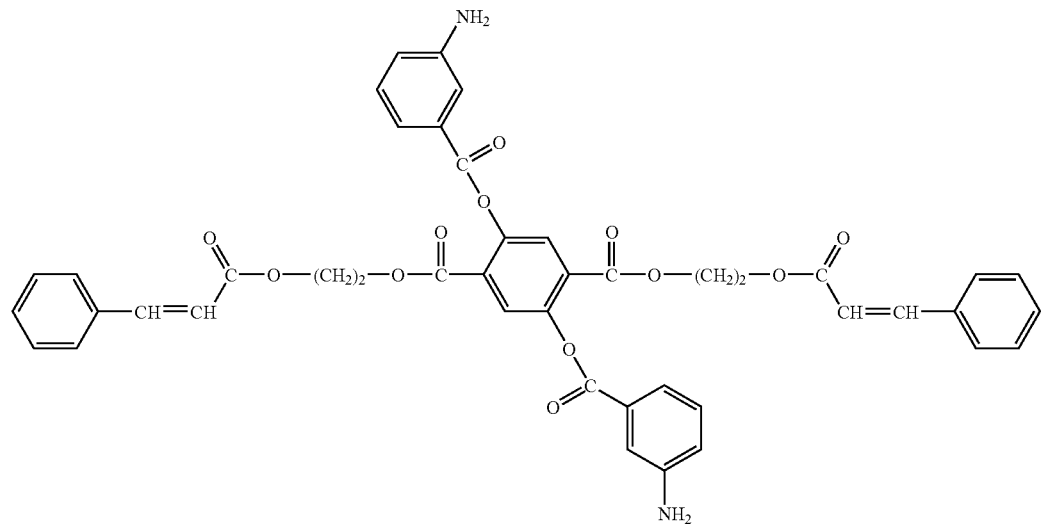
(12)
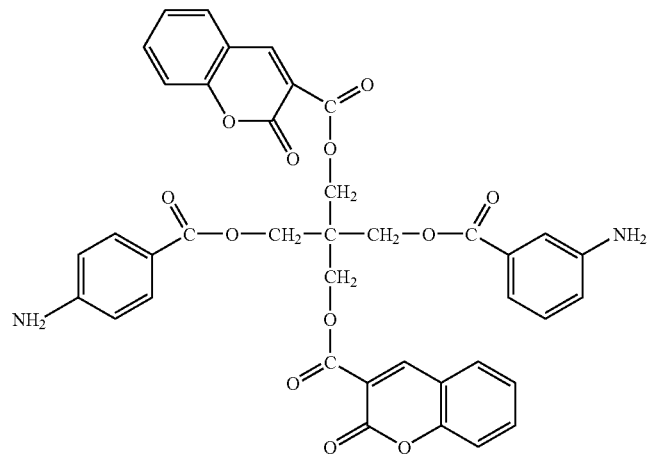
(13)
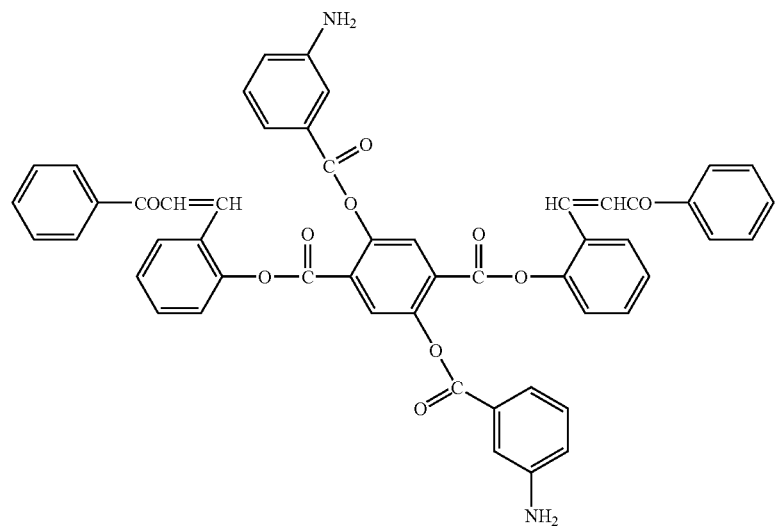

-continued (14)

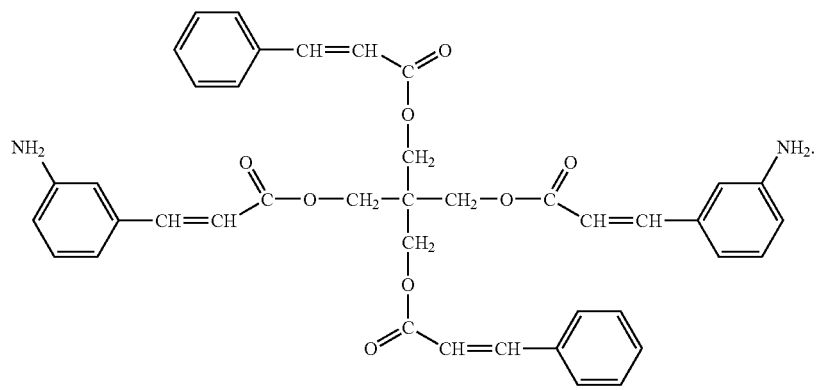

7. A diamine characterized by a structure represented by the general formula (3):

general formula (3)

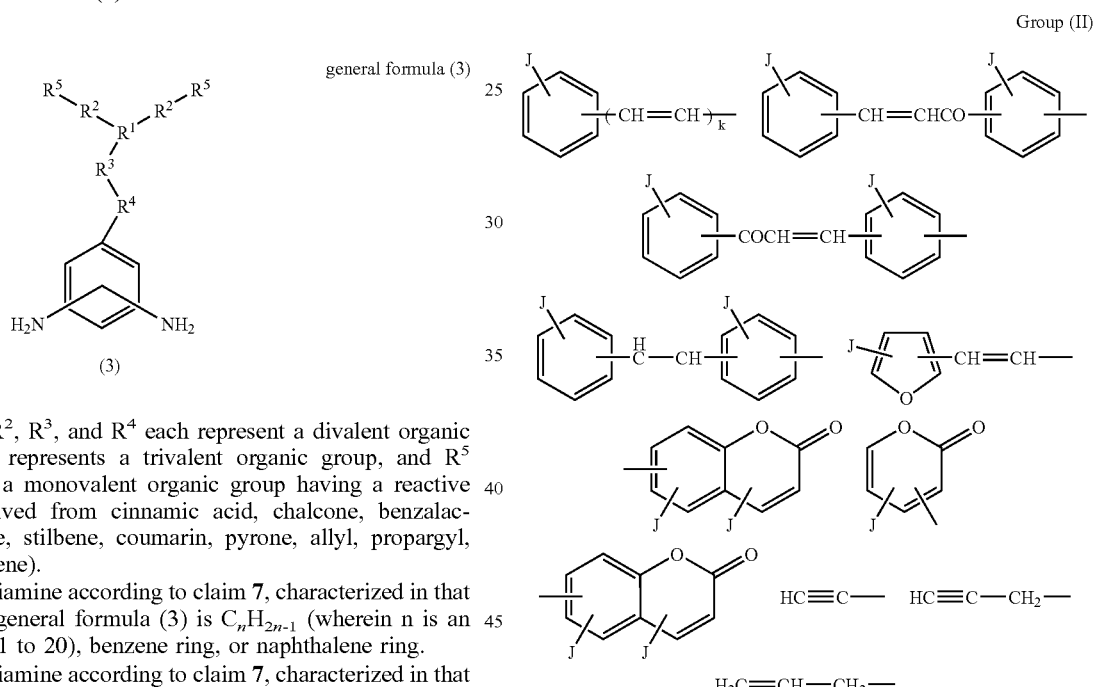

(3)

(wherein $R^2$, $R^3$, and $R^4$ each represent a divalent organic group, $R^1$ represents a trivalent organic group, and $R^5$ represents a monovalent organic group having a reactive group derived from cinnamic acid, chalcone, benzalacetophenone, stilbene, coumarin, pyrone, allyl, propargyl, and acetylene).

8. The diamine according to claim 7, characterized in that $R^1$ in the general formula (3) is $C_nH_{2n-1}$ (wherein n is an integer of 1 to 20), benzene ring, or naphthalene ring.

9. The diamine according to claim 7, characterized in that $R^2$ in the general formula a (3) is a single bond, —COO—, —MHCO—, —$(C_mH_{2m})$COO—, or —OCO $(C_mH_{2m})$COO— (wherein m is an integer of 2 to 20).

10. The diamine according to claim 7, wherein $R^3$ in the general formula (3) is a single bond or —COO— and $R^4$ is a single bond, —$CH_2$—, or —COO—.

11. The di amine according to claim 7, wherein $R^5$ in the general formula (3) includes a monovalent organic group selected from the group (II) consisting of (wherein J is a group capable of arbitrarily substituting for hydrogen atom of all aromatic ring and independently represents halogen, C1 to C3 alkyl, C1 to C3 alkoxy, or C1 to C3 fluoroalkyl, or a combination thereof).

* * * * *